(12) United States Patent
Goetz

(10) Patent No.: US 9,055,974 B2
(45) Date of Patent: Jun. 16, 2015

(54) IMPLANTABLE MEDICAL DEVICES STORING GRAPHICS PROCESSING DATA

(71) Applicant: Medtronic, Inc., Minneapolis, MN (US)

(72) Inventor: Steven M. Goetz, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/560,583

(22) Filed: Dec. 4, 2014

(65) Prior Publication Data

US 2015/0088093 A1 Mar. 26, 2015

Related U.S. Application Data

(62) Division of application No. 13/786,610, filed on Mar. 6, 2013, now Pat. No. 8,934,986, which is a division of application No. 13/086,991, filed on Apr. 14, 2011, now Pat. No. 8,406,890.

(51) Int. Cl.
*A61N 1/36* (2006.01)
*A61B 19/00* (2006.01)
*A61M 25/01* (2006.01)
(Continued)

(52) U.S. Cl.
CPC ........ *A61B 19/5244* (2013.01); *A61N 1/36128* (2013.01); *A61M 25/0105* (2013.01); *A61N 1/37235* (2013.01); *G06T 17/20* (2013.01); *A61B 2019/5236* (2013.01); *A61B 2019/524* (2013.01); *A61B 2019/5265* (2013.01); *A61M 2025/0166* (2013.01); *G06T 2210/41* (2013.01)

(58) Field of Classification Search
USPC ..................................... 607/59–60
See application file for complete search history.

(56) References Cited

U.S. PATENT DOCUMENTS 3,069,654 A 12/1962 Hough
5,241,472 A 8/1993 Gur et al.
(Continued)

FOREIGN PATENT DOCUMENTS

AU 709374 12/1997
WO 97/43871 11/1997
(Continued)

OTHER PUBLICATIONS

McIntyre et al., "Electric Field and Stimulating Influence Generated by Deep Brain Stimulation of the Subthalamic Nucleus," Clinical Neurophysiology, vol. 115, 2004, pp. 589-595.
(Continued)

*Primary Examiner* — Paula J Stice
(74) *Attorney, Agent, or Firm* — Shumaker & Sieffert, P.A.

(57) ABSTRACT

In one example, a device includes a telemetry module configured to retrieve graphics processing data from a device that is not configured to perform a rendering process using the graphics processing data and that is associated with delivering therapy to a therapy target of a patient, and a control unit configured to apply the graphics processing data while performing the rendering process to generate an image of an anatomical feature of the patient, wherein the anatomical feature comprises the therapy target for an implantable medical device, and to cause a display unit of a user interface to display the image, wherein the image of the anatomical feature is specific to the patient. The graphics processing data may include a list of vertices or a transform to be applied to a non-patient-specific anatomical atlas. The data may also include a location of a therapy element of the implantable medical device.

20 Claims, 14 Drawing Sheets

(51) Int. Cl.
*A61N 1/372* (2006.01)
*G06T 17/20* (2006.01)

(56) References Cited

U.S. PATENT DOCUMENTS

| | | |
|---|---|---|
| 5,722,999 A | 3/1998 | Snell |
| 6,026,142 A | 2/2000 | Gueziec et al. |
| 6,066,163 A | 5/2000 | John |
| 6,068,652 A | 5/2000 | Cohen et al. |
| 6,358,245 B1 | 3/2002 | Edwards et al. |
| 6,373,918 B1 | 4/2002 | Wiemker et al. |
| 6,393,325 B1 | 5/2002 | Mann et al. |
| 6,625,482 B1 | 9/2003 | Panescu et al. |
| 6,697,664 B2 | 2/2004 | Kienzle, III et al. |
| 6,993,384 B2 | 1/2006 | Bradley et al. |
| 7,044,942 B2 | 5/2006 | Jolly et al. |
| 7,239,920 B1 | 7/2007 | Thacker et al. |
| 7,239,926 B2 | 7/2007 | Goetz |
| 7,283,867 B2 | 10/2007 | Strother et al. |
| 7,346,382 B2 | 3/2008 | McIntyre et al. |
| 7,385,443 B1 | 6/2008 | Denison |
| 7,477,723 B2 | 1/2009 | Kamegawa et al. |
| 7,505,809 B2 | 3/2009 | Strommer et al. |
| 7,519,431 B2 | 4/2009 | Goetz et al. |
| 7,567,834 B2 | 7/2009 | Clayton et al. |
| 7,623,918 B2 | 11/2009 | Goetz |
| 7,831,307 B1 | 11/2010 | Moffitt |
| 7,983,757 B2 | 7/2011 | Miyazawa et al. |
| 8,160,328 B2 | 4/2012 | Goetz et al. |
| 8,288,628 B2 | 10/2012 | Larkins et al. |
| 8,406,890 B2 | 3/2013 | Goetz |
| 8,744,591 B2 | 6/2014 | Davis et al. |
| 8,934,986 B2 | 1/2015 | Goetz |
| 2003/0013977 A1 | 1/2003 | Daum |
| 2003/0139781 A1 | 7/2003 | Bradley et al. |
| 2004/0088027 A1 | 5/2004 | Burnes et al. |
| 2004/0098063 A1 | 5/2004 | Goetz |
| 2004/0210273 A1 | 10/2004 | Wang |
| 2004/0215239 A1 | 10/2004 | Favet et al. |
| 2005/0131474 A1 | 6/2005 | Jenkins et al. |
| 2005/0150418 A1 | 7/2005 | Bakeev et al. |
| 2005/0150535 A1 | 7/2005 | Samavedam et al. |
| 2005/0150734 A1 | 7/2005 | Breier et al. |
| 2005/0171587 A1 | 8/2005 | Daglow et al. |
| 2006/0122653 A1 | 6/2006 | Bradley et al. |
| 2006/0122654 A1 | 6/2006 | Bradley et al. |
| 2006/0195145 A1 | 8/2006 | Lee et al. |
| 2006/0217781 A1 | 9/2006 | John |
| 2007/0106360 A1 | 5/2007 | Gibson et al. |
| 2007/0129770 A1 | 6/2007 | Younis |
| 2007/0142888 A1 | 6/2007 | Chavez |
| 2007/0156136 A1 | 7/2007 | Godara et al. |
| 2007/0185544 A1 | 8/2007 | Dawant et al. |
| 2007/0203538 A1 | 8/2007 | Stone et al. |
| 2007/0203539 A1 | 8/2007 | Stone et al. |
| 2007/0203541 A1 | 8/2007 | Goetz et al. |
| 2007/0203543 A1 | 8/2007 | Stone et al. |
| 2007/0203545 A1 | 8/2007 | Stone et al. |
| 2007/0203546 A1 | 8/2007 | Stone et al. |
| 2007/0225674 A1 | 9/2007 | Molnar et al. |
| 2007/0255339 A1 | 11/2007 | Torgerson |
| 2007/0265489 A1 | 11/2007 | Fowler et al. |
| 2007/0288064 A1 | 12/2007 | Butson et al. |
| 2007/0288070 A1 | 12/2007 | Libbus et al. |
| 2008/0004675 A1 | 1/2008 | King et al. |
| 2008/0052312 A1 | 2/2008 | Tang et al. |
| 2008/0070521 A1 | 3/2008 | West et al. |
| 2008/0079362 A1 | 4/2008 | Kawakami et al. |
| 2008/0111523 A1 | 5/2008 | Kim |
| 2008/0154340 A1 | 6/2008 | Goetz et al. |
| 2008/0154341 A1 | 6/2008 | McIntyre et al. |
| 2008/0183256 A1 | 7/2008 | Keacher |
| 2008/0201037 A1 | 8/2008 | Suyama et al. |
| 2008/0218510 A1 | 9/2008 | Grass et al. |
| 2008/0269836 A1 | 10/2008 | Foffani et al. |
| 2008/0288029 A1 | 11/2008 | Healy et al. |
| 2009/0012416 A1 | 1/2009 | Belalcazar et al. |
| 2009/0082691 A1 | 3/2009 | Denison et al. |
| 2009/0083070 A1 | 3/2009 | Giftakis et al. |
| 2009/0099627 A1 | 4/2009 | Molnar et al. |
| 2009/0118635 A1 | 5/2009 | Lujan et al. |
| 2009/0118786 A1 | 5/2009 | Meadows et al. |
| 2009/0192556 A1 | 7/2009 | Wu et al. |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0228070 A1 | 9/2009 | Goetz et al. |
| 2009/0234422 A1 | 9/2009 | Goetz et al. |
| 2009/0276005 A1 | 11/2009 | Pless |
| 2009/0287273 A1 | 11/2009 | Carlton et al. |
| 2009/0306746 A1 | 12/2009 | Blischak |
| 2010/0100153 A1 | 4/2010 | Carlson et al. |
| 2010/0100154 A1 | 4/2010 | Roche |
| 2010/0135553 A1 | 6/2010 | Joglekar |
| 2011/0093030 A1 | 4/2011 | Goetz et al. |
| 2011/0093051 A1 | 4/2011 | Davis et al. |
| 2011/0144521 A1 | 6/2011 | Molnar et al. |
| 2011/0144715 A1 | 6/2011 | Molnar et al. |
| 2011/0264165 A1 | 10/2011 | Molnar et al. |
| 2011/0313487 A1 | 12/2011 | Kokones et al. |

FOREIGN PATENT DOCUMENTS

| | | |
|---|---|---|
| WO | 99/37358 | 7/1999 |
| WO | 01/54579 | 2/2001 |
| WO | 01/058351 A1 | 8/2001 |
| WO | 2006/110206 A1 | 10/2006 |
| WO | 2006/110690 A1 | 10/2006 |
| WO | 2007/007058 A1 | 1/2007 |
| WO | 2007/112061 A2 | 10/2007 |
| WO | 2009/055127 A1 | 4/2009 |
| WO | 2009/073891 A1 | 6/2009 |
| WO | 2009/134475 A1 | 11/2009 |
| WO | 2010/030904 A2 | 3/2010 |
| WO | 2010/044989 A2 | 4/2010 |

OTHER PUBLICATIONS

Freeman et al. "Determining the Minimum-Area Encasing Rectangle for an Arbitrary Closed Curve," Comm. ACM, Jul. 1975, pp. 409-413.

Lindeberg, "Feature Detection With Automatic Scale Selection," International Journal of Computer Vision 30 (2), 1998, pp. 79-116.

Lowe, "Distinctive Image Features from Scale-Invariant Keypoints," International Journal of Computer Vision 60 (2), 2004, pp. 91-110.

Lindeberg, "Detecting Salient Blob-Like Image Structures and Their Scales with a Scale-Space Primal Sketch: A Method for Focus-of-Attention," International Journal of Computer Vision 11 (3), 1993, pp. 283-318.

Jensen et al., "Information, Energy, and Entropy: Design Principles for Adaptive, Therapeutic Modulation of Neural Circuits," European Patent Office, Downloaded on Dec. 22, 2009, from IEEE Xplore (8 pgs.).

Chen et al., "Intra-operative recordings of local field potentials can help localize the subthalamic nucleus in Parkinson's disease surgery," Exp Neurol, (2005) (8 pgs.).

Debatisse et al., "DBS in STN and macrorecording using electrodes of stimulation: what can be done and where we are?," http://files.chuv.ch/internet-docs/nch/posters/nch_dbs_in_stn.pdf, (Jun. 13-17, 2005) (1 pg.).

Wingeier et al. "Intra-operative STN DBS attenuates the prominent beta rhythm in the STN in the STN in Parkinson's disease," Experimental Neurology 197 (2006) pp. 244-251.

Kühn et al., "High-Frequency Stimulation of the Subthalamic Nucleus Suppresses Oscillatory β Activity in Patients with Parkinson's Disease in Parallel with Improvement in Motor Performance," Journal of Neuroscience, 28(24), Jun. 11, 2008, pp. 6165-6173.

(56) References Cited

OTHER PUBLICATIONS

Marceglia et al., "Basal ganglia local field potentials: applications in the development of new deep brain stimulation devices for movement disorders," Expert Rev. Med. Devices 4(5), (2007) pp. 605-614.

Rossi et al., "Subthalamic local field potential oscillations during ongoing deep brain stimulation in Parkinson's disease," Brain Research Bulletin 76 (2008) pp. 512-521.

Yelnik et al., "Localization of stimulating electrodes in patients with Parkinson disease by using a three-dimensional atlas-magnetic resonance imaging coregistration method," J. Neurosurg. vol. 99, (2003) pp. 89-99.

Notification of Transmittal of the International Search Report and Written Opinion of the International Searching Authority for corresponding patent application No. PCT/US2012/027494, Nov. 9, 2012, 12 pages.

Prosecution History from U.S. Appl. No. 13/086,991, dated Aug. 30, 2012 through Mar. 6, 2013, 36 pp.

Prosecution History from U.S. Appl. No. 13/786,610, dated Mar. 6, 2014 through Oct. 2, 2014, 29 pp.

IMPLANTABLE MEDICAL DEVICES STORING GRAPHICS PROCESSING DATA

This application is a divisional of U.S. patent application Ser. No. 13/786,610, filed Mar. 6, 2013, which is a divisional of U.S. patent application Ser. No. 13/086,991, filed Apr. 14, 2011, the entire contents of both applications are hereby incorporated by reference.

TECHNICAL FIELD

This disclosure relates to implantable medical devices (IMDs), and, more particularly, to processing of images used in conjunction with IMDs.

BACKGROUND

A variety of implantable medical devices (IMDs) are used for chronic, i.e., long-term, delivery of therapy or diagnostic monitoring to patients suffering from a variety of conditions, such as cardiac dysfunction, chronic pain, tremor, Parkinson's disease, epilepsy, urinary or fecal incontinence, sexual dysfunction, obesity, spasticity, or gastroparesis. As examples, electrical stimulation generators are used for chronic delivery of electrical stimulation therapies such as cardiac pacing, cardiac cardioversion/defibrillation, neurostimulation, muscle stimulation, or the like. Pumps or other fluid delivery devices may be used for chronic delivery of therapeutic fluids, such as drugs, proteins, growth factors, pain relief agents or genetic agents. Typically, such devices provide therapy continuously or periodically according to parameters contained within a program. A program may comprise respective values for each of a plurality of parameters, specified by a clinician. The devices may receive the program from a programmer controlled by the clinician.

Examples of such implantable medical devices include implantable fluid delivery devices, implantable neurostimulators, implantable cardioverters, implantable cardiac pacemakers, implantable cardioverter-defibrillators, and cochlear implants. Typically, such devices are implanted in a patient to deliver therapy to or measure a signal from a target site within the patient under specified conditions on a recurring basis.

For example, an implantable fluid delivery device may be implanted at a location in the body of a patient and deliver a fluid medication through a catheter to a selected delivery site in the body. Similarly, an implantable electrical stimulator can be implanted to deliver electrical stimulation therapy to a patient at a selected site. For example, an implantable electrical stimulator delivers electrical therapy to a target tissue site within a patient with the aid of one or more medical leads that include electrodes. An electrical stimulator may deliver therapy to a patient via selected combinations of electrodes.

Precise placement of a lead or catheter, or at least knowledge of positioning of the lead or catheter, may be helpful in programming and delivering therapy. As one example, knowledge of the positions of electrodes carried by one or more leads may be helpful in formulating efficacious therapy, both upon implantation and over the course of therapy following implantation. As another example, the position of the distal outlet of a catheter may be helpful in determining proximity to a therapeutic target, both upon implantation and over the course of therapy following implantation. Knowledge of the location of a device element may further aid in the interpretation of sensed physiologic data.

SUMMARY

In general, this disclosure describes techniques for storing data for reproducing an image of an anatomical feature of a patient. The techniques of this disclosure are directed to producing a patient-specific image, that is, an image of the anatomical feature of the patient as it exists within the patient. The image may include a representation of a therapy element, such as a lead or a catheter, at the location of the anatomical feature at which the therapy element is implanted.

Rather than storing image data itself (or an encoded representation of the image data), the techniques of this disclosure are directed to storing graphics processing data that can be applied during a rendering process to reproduce the image. In this manner, a clinician may view the details of the anatomical feature specific to the patient, as well as the location of the therapy element within the patient relative to the anatomical feature, to monitor and/or adjust the therapy delivered by an implantable medical device coupled to the therapy element.

In one example, an implantable medical device includes a memory configured to store data for a program of the implantable medical device, a therapy unit configured to perform at least one of delivery of therapy and sensing of a physiological signal at a therapy target of an anatomical feature of a patient, and an interface configured to receive the data for the program and to store the data for the program to the memory, wherein the interface is further configured to receive graphics processing data comprising data that, when applied during a rendering process, produces an image of the anatomical feature of the patient, wherein the implantable medical device is not configured to perform the rendering process using the graphics processing data.

In another example, a method includes retrieving graphics processing data from a device that is not configured to perform a rendering process using the graphics processing data, wherein the device is associated with at least one of delivering therapy and sensing a physiological signal at a therapy target of a patient, applying the graphics processing data while performing the rendering process to generate an image of an anatomical feature of the patient, wherein the anatomical feature comprises the therapy target for an implantable medical device, and displaying the image, wherein the image of the anatomical feature is specific to the patient.

In another example, a device includes a telemetry module configured to retrieve graphics processing data from a device that is not configured to perform a rendering process using the graphics processing data and that is associated with at least one of delivering therapy and sensing a physiological signal at to a therapy target of a patient, and a control unit configured to apply the graphics processing data while performing the rendering process to generate an image of an anatomical feature of the patient, wherein the anatomical feature comprises the therapy target for an implantable medical device, and to cause a display unit of a user interface to display the image, wherein the image of the anatomical feature is specific to the patient.

In another example, a computer-readable medium, such as a computer-readable storage medium, contains, e.g., is encoded with, instructions that, when executed, cause a processor to retrieve graphics processing data from a device that is not configured to perform a rendering process using the graphics processing data, wherein the device is associated with at least one of delivering therapy and sensing a physiological signal at a therapy target of a patient, apply the graphics processing data while performing the rendering process to generate an image of an anatomical feature of the patient, wherein the anatomical feature comprises the therapy target for an implantable medical device, and cause a display unit comprising a user interface to display the image, wherein the image of the anatomical feature is specific to the patient.

In another example, a system includes an implantable medical device and an image manipulation device. The implantable medical device includes a memory that stores graphics processing data, wherein the implantable medical device is configured to at least one of deliver therapy and sense a physiological signal at a therapy target of a patient, and wherein the implantable medical device is not configured to perform a rendering process using the graphics processing data. The image manipulation device is configured to retrieve the graphics processing data from the memory of the implantable medical device, and to perform the rendering process, to apply the graphics processing data while performing the rendering process to generate an image of an anatomical feature of the patient, wherein the anatomical feature comprises the therapy target for the implantable medical device, and to cause a user interface of a display unit to display the image, wherein the image of the anatomical feature is specific to the patient.

In another example, a method includes obtaining information representative of an anatomical feature of a patient, wherein the anatomical feature comprises a therapy target for an implantable medical device, determining graphics processing data based on the obtained information, wherein the graphics processing data comprises data that, when applied during a rendering process, produces an image of the anatomical feature of the patient, and storing the graphics processing data to a device that is not configured to perform the rendering process using the graphics processing data, wherein the device is associated with at least one of delivering therapy and sensing a physiological signal at the therapy target of the patient.

In another example, a device includes an interface configured to obtain information representative of an anatomical feature of a patient, wherein the anatomical feature comprises a therapy target for an implantable medical device, and a control unit configured to determine graphics processing data based on the obtained information, wherein the graphics processing data comprises data that, when applied during a rendering process, produces an image of the anatomical feature of the patient, and store the graphics processing data to a device that is not configured to perform the rendering process using the graphics processing data, wherein the device is associated with at least one of delivering therapy and sensing a physiological signal at the therapy target of the patient.

In another example, a computer-readable medium includes instructions that, when executed, cause a processor to obtain information representative of an anatomical feature of a patient, wherein the anatomical feature comprises a therapy target for an implantable medical device, determine graphics processing data based on the obtained information, wherein the graphics processing data comprises data that, when applied during a rendering process, produces an image of the anatomical feature of the patient, and store the graphics processing data to a device that is not configured to perform the rendering process using the graphics processing data, wherein the device is associated with at least one of delivering therapy and sensing a physiological signal at the therapy target of the patient.

In another example, an implantable medical device includes a therapy unit configured to perform at least one of delivery of a therapy and measurement of physiologic signals at a therapy target of an anatomical feature of a patient, and a memory comprising stored data for a program of the implantable medical device and graphics processing data, wherein the graphics processing data comprises data that, when applied during a rendering process, produces an image of the anatomical feature of the patient, wherein the implantable medical device is not configured to perform the rendering process using the graphics processing data.

The details of one or more examples are set forth in the accompanying drawings and the description below. Other features, objects, and advantages will be apparent from the description and drawings, and from the claims.

DETAILED DESCRIPTION

Figure 1:
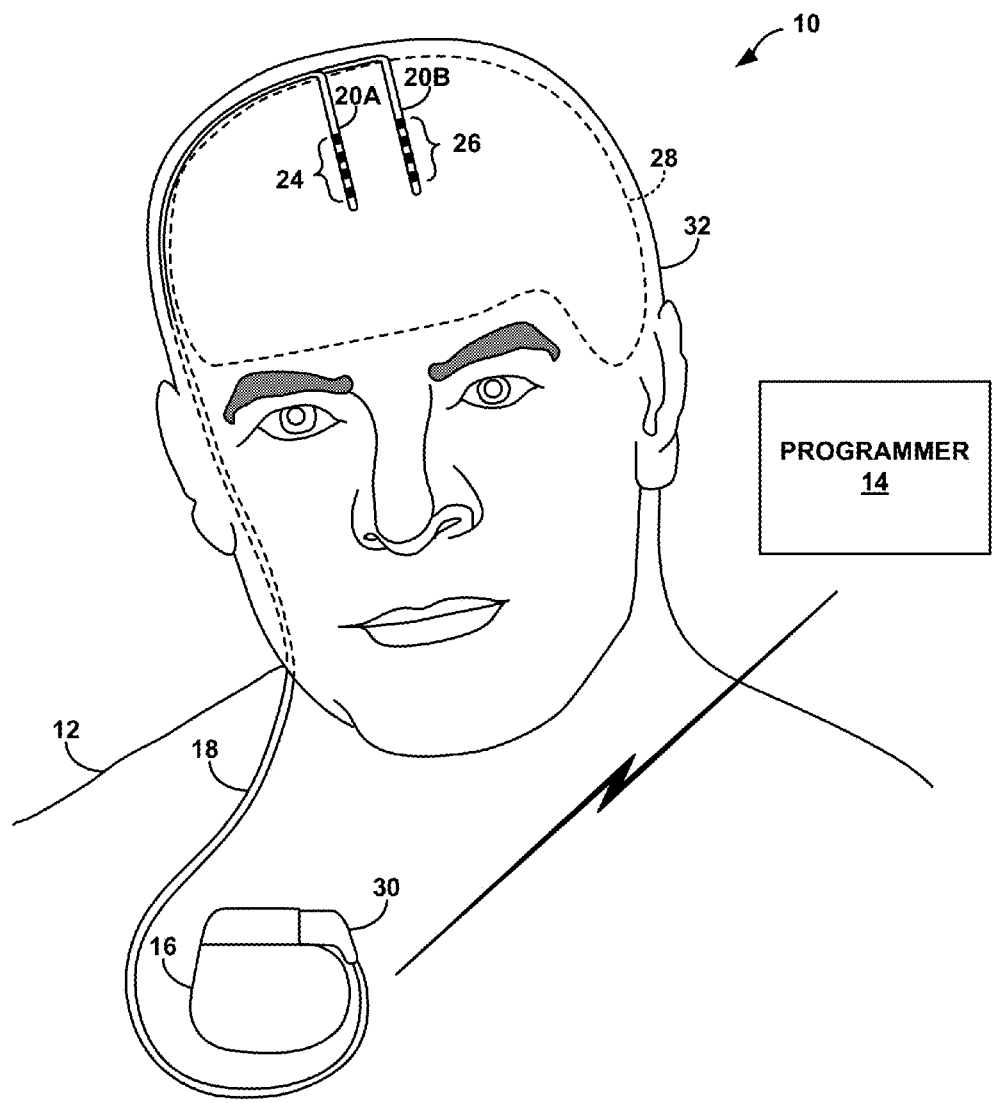
FIG. 1 is a conceptual diagram illustrating an example therapy system that delivers therapy to manage a patient condition.

This disclosure describes techniques for producing a patient-specific image, that is, an image of an anatomical feature of the patient as the anatomical feature exists within the patient. The image may include a representation of a therapy element, such as a lead, a leadless stimulator, or a catheter, at the location of the anatomical feature at which the therapy element is implanted. Rather than storing image data itself (or an encoded representation of the image data), the techniques of this disclosure are directed to storing graphics processing data that can be applied during a rendering process to produce the image.

The phrase "graphics processing data" as used in this disclosure refers to data that is rendered or applied during a rendering process. The term "render" is intended to refer to the process of producing pixel data, which is to be displayed as a two-dimensional image, or a set of images arranged so as to create a three dimensional effect, by a display device such as a computer monitor, from graphics objects, which may comprise two-dimensional or three-dimensional graphics objects. Graphics objects include graphics primitives, such as points, lines, triangles, rectangles, and other polygons, as well as structures made up of multiple primitives, such as, for example, three-dimensional meshes.

The rendering process is performed to generate pixel data, such as values for red-green-blue triplet values for each pixel of an image, from the graphics objects. In this manner, the rendering process referred to by this disclosure is distinct from, for example, decoding an encoded representation of an image, such as decoding a Joint Photographic Experts Group (JPEG) encoded image. That is, whereas decoding an encoded image generally includes decoding encoded pixel data or other data generally representative of pixels of an image, a rendering process generally includes generating pixel data from a higher-order representation of data, such as two- or three-dimensional graphics objects (e.g., graphics primitives), which may, in some examples, further take into account camera viewpoint, lighting effects, and other such factors. Though portions of the image actually displayed following the rendering process may result from decoding an encoded image, at least some portion of the displayed image is generated from graphics processing data, e.g., by applying the graphics processing data during a rendering process, in accordance with the techniques of this disclosure.

The techniques of this disclosure may include generating a three-dimensional model of an anatomical feature, including a therapy target, for a patient. The model of the anatomical feature may be patient-specific. For example, an image manipulation device may receive data from an imaging device, such as a magnetic resonance imaging (MRI) machine, a computed tomography (CT) machine, a fluoroscopic imaging machine, or an ultrasound imaging machine, that captures images of the anatomical feature of the patient. The image manipulation device may then construct a patient-specific model of the anatomical feature of the patient. The images used to construct the model may be captured after implanting an implantable medical device in the patient, such that the images include a representation of a lead or catheter (generally referred to herein as a "therapy element") of the implantable medical device at the anatomical feature.

In particular, the techniques of this disclosure are directed to storing and retrieving graphics processing data to and from devices associated with delivering therapy to patients, but that are not themselves configured to perform the rendering process using the graphics processing data. In some examples, these techniques include storing the graphics processing data to an implantable medical device. In some examples, these techniques include storing the graphics processing data to a patient programmer associated with the implantable medical device. In each case, the device may store graphics processing data for use by a different device, such as a clinician programmer or other computing device.

The graphics processing data, as noted above, may be applied during a rendering process to generate an image of the patient-specific anatomical feature of the patient. In some examples, a three-dimensional mesh of the anatomical feature of the patient is created. The three-dimensional mesh may be constructed from a plurality of graphics primitives, e.g., triangles. Graphics primitives are typically defined using a list of vertices. For example, a triangle graphics primitive is defined using three vertices. Accordingly, the graphics processing data may comprise a list of vertices for graphics primitives corresponding to the three-dimensional mesh. The list of vertices may also be referred to as a "vertex array." Accordingly, applying the graphics processing data during the rendering process may include rendering a graphics object defined by the graphics processing data, in some examples.

In some examples, the graphics processing data may include one or more transforms, also referred to as "transform functions" or "transform matrices." Transforms can be applied to a model (such as an anatomical atlas) to manipulate the model, e.g., to translate the model (e.g., move vertices of the model along a specified vector), rotate the model (e.g., rotate vertices of the model about a vector), or scale the model (e.g., increase or decrease distance between vertices of the model to change the size of the model along one or more axes). In these examples, a patient-specific model may be compared to an anatomical atlas. The anatomical atlas model may define a general (non-patient-specific) model of the anatomical feature, e.g., representative of a median for a general population of patients. The techniques of this disclosure include calculating one or more transforms that, when applied to the anatomical atlas model, yield a model that substantially conforms to the patient-specific model of the anatomical feature. In this manner, the transforms may be used to represent differences between the patient-specific model and the anatomical atlas model. The transforms may be applied during the rendering process. That is, the anatomical atlas model may be transformed by the one or more transforms to produce a model, which is rendered to produce a patient-specific image of the anatomical feature of the patient. In this manner, applying the graphics processing data during the rendering process may include transforming an anatomical model using transforms defined by the graphics processing data, in some examples.

It is not uncommon for patients to visit various clinical care centers during treatment. Even when a patient returns to the same care center, the care center may include a variety of different clinician programmer devices, or other general computing devices, which may be spread across locations or users. By storing the graphics processing data to a device associated with delivering therapy to a patient, the techniques of this disclosure may ensure that a clinician is able to view an image of an anatomical feature of the patient, so long as the patient is near the clinician. For example, the clinician may use a clinician programmer (also referred to as a physician programmer) or other computing device to retrieve the graphics processing data from the device associated with delivering therapy to a patient, e.g., an implantable medical device or a patient programmer device. After the clinician programmer retrieves the graphics processing data, the clinician programmer may perform the rendering process, applying the graphics processing data during the rendering process, to produce a patient-specific image of the anatomical feature of the patient being treated by the implantable medical device. Accordingly, the clinician may then have access to a patient-specific image, which may more accurately reflect the patient's physiology than a more general anatomical atlas.

Moreover, the graphics processing data may consume less memory than stored image data itself, or even an encoded representation of the image data. For example, stored image data for a head scan MRI may consume 20-30 Mbytes of data of data. Higher resolution scans or scans of larger body areas can increase storage size significantly. On the other hand, a stored list of vertices, in accordance with the techniques of this disclosure, may consume approximately 45 kilobytes of data, assuming a relatively high polygon count of 650 triangles defined by 1950 vertices. This data could be optimized, e.g., by reducing the precision of the vertices, to produce a list of vertices consuming only tens of kilobytes. Likewise, a stored transform may consume only tens of hundreds of bytes of data. Even storing multiple transforms, e.g., individual transforms per brain hemisphere or even per anatomical structure, may yield data of less than a full kilobyte. Accordingly, the techniques of this disclosure may provide advantages in terms of the amount of data stored by an implantable medical device and/or patient programmer device. Because the graphics processing data can be represented using a lower amount of data, the time required to download the graphics processing data to an implantable medical device, e.g., via wireless telemetry, may be significantly reduced over storing an image to the implantable medical device.

The techniques of this disclosure may also provide advantages over storing images on a remote server. In some cases, a clinical care center may not have access to a remote server, e.g., due to Internet connectivity being unavailable or due to restrictions that may block hardware not managed by clinic or hospital staff. Also, storing data to a device associated with delivering therapy to a patient, such as an implantable medical device or patient programmer, may reduce privacy concerns that may arise by storing patient data on a remote server.

Programmable implantable medical devices are typically programmed using an external programming device, sometimes known as a controller or programmer, which can communicate with the implanted medical device through well-known techniques such as wireless telemetry. An external controller, or programmer, can be used by a medical professional, for example, to change the therapeutic regimen by increasing or decreasing the amount of fluid medication delivered to the patient, in the case of fluid delivery therapy, or changing electrode stimulation patterns, in the case of electrical stimulation. Typically, a medical professional interacts with the external controller or programmer to set various parameters associated with the implantable medical device and then transmits, or downloads, those parameters to the implanted medical device. The external device may also record other information important to the delivery of the therapy. Some information may be stored in the implantable medical device and/or the external programming device. Such information may include patient information, implanted device information such as model, volume, implant location, length of catheter or lead, and other information specific to different devices.

During a programming session, which may occur during implant of the medical device, during a trial session, or during a follow-up session after the medical device is implanted in the patient, a clinician may generate one or more therapy programs that provide efficacious therapy to the patient, where each therapy program may define values for a set of therapy parameters. The clinician may refer to a patient-specific image of an anatomical feature of the patient, which may include a representation of the lead or catheter placement in a therapy target of the anatomical feature, while programming the device.

FIG. 1 is a conceptual diagram illustrating an example therapy system 10 that delivers therapy to manage a patient condition, such as a movement disorder, neurodegenerative impairment, a mood disorder or a seizure disorder of patient 12. Patient 12 ordinarily will be a human patient. In some cases, however, therapy system 10 may be applied to other mammalian or non-mammalian, non-human patients. While movement disorders and neurodegenerative impairment are primarily referred to herein, in other examples, therapy system 10 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, dysthymic disorder or obsessive-compulsive disorder (OCD)).

Therapy system 10 includes medical device programmer 14, implantable medical device (IMD) 16, lead extension 18, and leads 20A and 20B with respective sets of electrodes 24, 26. In the example shown in FIG. 1, electrodes 24, 26 of leads 20A, 20B (collectively referred to as "leads 20"), respectively, are positioned to deliver electrical stimulation to a tissue site within brain 28, such as a deep brain site under the dura mater of brain 28 of patient 12. In this example, IMD 16 provides deep brain stimulation (DBS) therapy. In other examples, IMD 16 may provide other therapies, such as, for example, spinal cord stimulation, pelvic floor stimulation, gastric stimulation, occipital nerve stimulation, cardiac stimulation, intrathecal drug delivery, intraparenchymal drug delivery, intracerebroventricular drug delivery, pelvic floor drug delivery, and the like.

Although the example of FIG. 1 illustrates leads 20, in other examples, IMD 16 may be configured to deliver other types of therapy. For example, IMD 16 may comprise an implantable drug pump in some examples. In such examples, rather than being coupled to leads such as leads 20, IMD 16 would be coupled to one or more catheters. This disclosure generally refers to the item coupled to IMD 16 by which IMD 16 delivers therapy (e.g., stimulation therapy or chemical therapy) to a therapy target of patient 12 as a therapy element, although the coupled item may also measure physiologic signals in addition to or instead of delivering therapy. Accordingly, in various examples, the therapy element may comprise one or more leads or one or more catheters. For purposes of example, the discussion of FIG. 1 refers to the specific example of leads 20. However, it should be understood that the techniques of this disclosure may also be applied when the therapy element of IMD 16 comprises, e.g., a catheter.

In some examples, delivery of stimulation to one or more regions of brain 28, such as the subthalamic nucleus (e.g., the dorsal subthalamic nucleus), globus pallidus, internal capsule, thalamus or motor cortex, may be an effective treatment to mitigate or even eliminate one or more symptoms of movement disorders. A movement disorder or other neurodegenerative impairment may include symptoms such as, for example, muscle control impairment, motion impairment or other movement problems, such as rigidity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

Electrodes 24, 26 of leads 20 may also be positioned to sense bioelectrical brain signals within brain 28 of patient 12. In some examples, some of electrodes 24, 26 may be configured to only sense bioelectrical brain signals and other electrodes 24, 26 may be configured to only deliver electrical stimulation to brain 28. In other examples, some or all of electrodes 24, 26 are configured to both sense bioelectrical brain signals and deliver electrical stimulation to brain 28.

IMD 16 includes a therapy module that includes a stimulation generator that generates and delivers electrical stimulation therapy to patient 12 via a subset of electrodes 24, 26 of leads 20A and 20B, respectively. The subset of electrodes 24, 26 includes at least one electrode and can include a plurality of electrodes. The subset of electrodes 24, 26 that are used to deliver electrical stimulation to patient 12, and, in some cases, the polarity of the subset of electrodes 24, 26, may be referred to as a stimulation electrode combination or configuration. In some examples, the stimulation electrode combination includes a first electrode positioned on a lead 20A or 20B and a reference electrode positioned relatively far from the first electrode (e.g., unipolar stimulation) or two or more electrodes positioned on one or more leads 20A, 20B (e.g., bipolar stimulation).

The stimulation electrode combination can be selected for a particular patient 12 and patient condition based on a bioelectrical brain signal sensed within brain 28 of patient 12 and a physiological model (which is specific to an anatomical feature, such as brain 28, of patient 12) that is based on placement of electrodes of leads 20 within the brain of the patient. The physiological model can be generated by a computing device (e.g., a medical data computing device implemented in a general purpose computer or a medical device programmer) executing instructions defining an algorithm that references a location of leads 20 within brain 28 relative to patient anatomy data. The locations of leads 20 can be determined using any suitable technique, such as based on a medical image generated using any suitable imaging modality (e.g., computed tomography (CT), magnetic resonance imaging (MRI), x-ray or fluoroscopy), based on the stereotactic coordinates used to implant leads 20 within brain 28, based on correlations of signals sensed by IMD 16 with anatomical structures expected to yield those signals, correlations of stimulation effects at electrodes with anatomical structures expected to yield those effects, or based on a clinician-estimated location of leads 20 within brain 28.

In other examples, the stimulation electrode combination can be selected for a particular patient 12 and patient condition based on a bioelectrical brain signal sensed within brain 28 of patient 12 and a physiological model that is based on placement of electrodes of another medical member, such as a leadless electrical stimulator. Thus, although described with respect to electrodes of leads 20, the devices, systems, and techniques described herein can also be used to select a stimulation electrode combination based on placement of electrodes within brain 28 of patient 12, regardless of the type of component to which the electrodes are coupled. In such examples, the physiological model can be generated by a computing device (executing instructions defining an algorithm that references a location of the electrodes (or the medical member comprising the electrodes) within brain 28 relative to patient anatomy data. The location of the electrodes or medical component can be determined using any suitable technique, such as the techniques described with respect to leads 20.

Patient anatomy data indicates one or more characteristics of patient tissue proximate to implanted leads 20, such as one or more anatomical structures proximate implanted leads 20. The patient anatomy data may include at least one of an anatomical image of a patient, a reference anatomical image, an anatomical atlas, a tissue conductivity data set, or a data set containing parameters of fluid dynamics governing distribution of an infused agent. The patient anatomy data may be specific to patient 12 or may represent data for more than one patient, e.g., model or averaged data of the anatomical structure and tissue conductivity of multiple patients. For example, in some examples, the patient anatomy data may include tissue conductivity data or other relevant tissue data that is typical for the particular lead 20 location for the particular therapeutic application (e.g., deep brain stimulation in the case of FIG. 1), and may be, but need not be, specific to patient 12. Such data may consist of regions of anatomy that are associated with beneficial therapeutic effects (target volumes') or regions that are associated with negative outcomes (side effect volumes') as determined by analysis of population data sets. In some examples, the computing device generates the patient anatomy data from an imaging modality, such as, but not limited to, CT, MRI, x-ray, fluoroscopy, and the like.

In some examples, the bioelectrical signals sensed within brain 28 may reflect changes in electrical current produced by the sum of electrical potential differences across brain tissue. Examples of bioelectrical brain signals include, but are not limited to, electrical signals generated from local field potentials (LFP) sensed within one or more regions of brain 28, such as an electroencephalogram (EEG) signal, or an electrocorticogram (ECoG) signal. Local field potentials, however, may include a broader genus of electrical signals within brain 28 of patient 12.

In some examples, the bioelectrical brain signals that are used to select a stimulation electrode combination may be sensed within the same region of brain 28 as the target tissue site for the electrical stimulation or a different region of brain 28. As previously indicated, these tissue sites may include tissue sites within the thalamus, subthalamic nucleus (STN) or globus pallidus of brain 28, as well as other target tissue sites (e.g., other basal ganglia structures). The specific target tissue sites and/or regions within brain 28 may be selected based on the patient condition. Thus, in some examples, both a stimulation electrode combination and sense electrode combinations may be selected from the same set of electrodes 24, 26. In other examples, the electrodes used for delivering electrical stimulation may be different than the electrodes used for sensing bioelectrical brain signals.

A processor of therapy system 10 accesses data for a physiological model from, e.g., a memory of therapy system 10, which can be a memory of programmer 14, IMD 16 or a memory of another device (e.g., a database remotely located from programmer 14 or IMD 16 that stores one or more physiological models). In accordance with the techniques of this disclosure, IMD 16 and/or programmer 14 may store graphics processing data for the physiological model. The physiological model may be generated by a different computing device and stored in the memory. The physiological model may be specific to patient 12. For example, the stored physiological model may be generated based on placement of leads 20 and electrodes 24, 26 within brain 28 of patient 12.

In some examples, the processor generates a physiological model based on a placement of leads 20 and electrodes 24, 26 within brain 28. The physiological model can be generated with the aid of modeling software, hardware, or firmware executing on a computing device, such as programmer 14 or a separate dedicated or multifunction computing device. In some examples, the processor displays an image representative of the physiological model on a user interface of a display in order to provide information that guides a clinician in the selection of the stimulation electrodes. In other examples, the computing device provides a stimulation electrode combination recommendation based on the physiological model generated based on the location of lead 20 and the patient anatomy data.

In some examples, the physiological model comprises a graphical representation of a therapy field that represents a region of the patient's tissue to which therapy is delivered. For example, the therapy field can include an electrical stimulation field (also referred to as an electrical field) that is generated when IMD 16 delivers electrical stimulation to brain 28 of patient 12 via a selected subset of electrodes 24, 26 and a therapy program defining stimulation parameters. The electrical field represents the region of tissue that will be covered by an electrical field (e.g., an electrical field or an electromagnetic field) during therapy. In other examples, the therapy field can be an activation field, which indicates the neurons that will be activated by the electrical field in the patient anatomical region covered by the stimulation therapy, thereby indicating the tissue area activated by the electrical stimulation delivered via the specific therapy program, which includes a selected subset of electrodes 24, 26 and other stimulation parameter values (e.g., current or voltage amplitude value and/or frequency value). Another type of therapy field model is a voltage gradient or a current density model that indicates the voltage gradient or current density of an electrical field generated when IMD 16 delivers electrical stimulation to brain 28 of patient 12 via a selected subset of electrodes 24, 26 and a particular set of therapy parameter values. Yet another type of therapy field model may relate to regions in which an infusion agent is distributed at a concentration sufficient to yield efficacious effect.

In other examples, the physiological model includes graphics processing data for producing a graphical representation of the one or more anatomical structures of brain 28 proximate the implanted leads 20, and, in some examples, also includes graphics processing data for producing a graphical representation of leads 20. The graphics processing data for producing the graphical representation of leads 20 may correspond to a point representative of a distal tip of a lead and an angle of the lead relative to the point, two points defining the lead, parameters defining one or more curves along which the lead traverses, and/or points representative of centers of electrodes along the lead. In some examples, the physiological model is determined based on the actual implant site of leads 20 within brain 28. For example, a processor of a computing device (e.g., programmer 14 or another computing device) can implement an algorithm that maps the 3D coordinates (e.g., stereotactic coordinates) of electrodes 24, 26 within brain 28 to an anatomical image of brain 28 to determine and display the anatomical structures proximate implanted electrodes 24, 26.

The 3D coordinates can be the coordinates with which leads 20 were implanted in brain 28 or coordinates provided by a clinician that estimate the location of leads 20 within brain 28. The location of the anatomical structures within brain 28 can be determined based on patient anatomy data specific to patient 12. For example, the physiological model that includes the graphical representation of the anatomical structures of brain 28 can be rendered to display an image of at least a portion of brain 28 of patient 12. In some examples, the physiological model can be produced by applying one or more transforms stored within IMD 16 to an anatomical atlas, also referred to as an anatomical atlas model or an atlas model in this disclosure, and the transforms may be stored within IMD 16.

In some examples, programmer 14 or another computing device can generate the physiological model and display a rendered version of the physiological model on a display of a user interface. The clinician can then determine, based on the image of the physiological model, whether the electrodes of the sense or stimulation electrode combination are proximate the target anatomical structures or the anatomical structures to be avoided.

After selecting stimulation electrode combinations, a clinician, alone or with the aid of a computing device, such as programmer 14, may select the other stimulation parameter values that provide efficacious therapy to patient 12. These other stimulation parameter values may include, for example, a frequency and amplitude of stimulation signals, and, in the case of stimulation pulses, a duty cycle, pulse width of the stimulation signals, and an electrode configuration (e.g., selected combination and polarities) of electrodes. In other cases, programmer 14 may suggest information about the stimulation waveform as well as pattern of delivered stimulation pulses.

In some examples, after IMD 16 is implanted within patient 12 and programmed for chronic therapy delivery, IMD 16 may periodically reassess the selected stimulation electrode combination to determine whether another stimulation electrode combination may provide more efficacious therapy. IMD 16 may determine, for example, whether the target tissue site for stimulation therapy has changed based on physiological changes in brain 28 or whether one or both leads 20A, 20B have migrated away from the original implant site within brain 28, or whether the leads have migrated relate to one another.

In order to assess the selected stimulation electrode combination based on the physiological model, a clinician can obtain a medical image of leads 20 and respective electrodes 24, 26 using any suitable imaging modality. Programmer 14 or another computing device can generate the physiological model based on the location of electrodes 24, 26 indicated by the medical image and patient anatomy data. The physiological model can indicate, for example, whether the selected stimulation electrodes are still positioned to deliver electrical stimulation to the one or more target anatomical structure and/or avoid the one or more anatomical structures associated with a stimulation-induced side effect. For example, the physiological model can indicate whether the electrical field, activation field, voltage gradient or current density of the therapy field resulting from stimulation delivery via the selected stimulation electrode combination is still targeting the target anatomical structures and/or avoiding the anatomical structures associated with stimulation-induced side effects.

Electrical stimulation generated by IMD 16 may be configured to manage a variety of disorders and conditions. In some examples, the stimulation generator of IMD 16 is configured to generate and deliver electrical pulses to patient 12 via electrodes of a selected stimulation electrode combination. However, in other examples, the stimulation generator of IMD 16 may be configured to generate and deliver a continuous wave signal, e.g., a sine wave or triangle wave. In either case, a signal generator within IMD 16 may generate the electrical stimulation therapy for DBS according to a therapy program that is selected at that given time in therapy. In examples in which IMD 16 delivers electrical stimulation in the form of stimulation pulses, a therapy program may include a set of therapy parameter values, such as a stimulation electrode combination for delivering stimulation to patient 12, pulse frequency, pulse width, and a current or voltage amplitude of the pulses. As previously indicated, the stimulation electrode combination may indicate the specific electrodes 24, 26 that are selected to deliver stimulation signals to tissue of patient 12 and the respective polarity of the selected electrodes.

IMD 16 may be implanted within a subcutaneous pocket above the clavicle, or, alternatively, the abdomen, back or buttocks of patient 12, on or within cranium 32 or at any other suitable site within patient 12. Generally, IMD 16 is constructed of a biocompatible material that resists corrosion and degradation from bodily fluids. IMD 16 may comprise a hermetic housing to substantially enclose components, such as a processor, therapy module, and memory.

As shown in FIG. 1, implanted lead extension 18 is coupled to IMD 16 via connector 30 (also referred to as a connector block or a header of IMD 16). In the example of FIG. 1, lead extension 18 traverses from the implant site of IMD 16 and along the neck of patient 12 to cranium 32 of patient 12 to access brain 28. In the example shown in FIG. 1, leads 20A and 20B (collectively "leads 20") are implanted within the right and left hemispheres, respectively, of patient 12 in order to deliver electrical stimulation to one or more regions of brain 28, which may be selected based on the patient condition or disorder controlled by therapy system 10. The stimulation electrodes used to deliver stimulation to the target tissue site may be selected based on one or more sensed bioelectrical brain signals and a physiological model that indicates a region of brain 28 proximate the implanted electrodes. Other lead 20 and IMD 16 implant sites are contemplated. For example, IMD 16 may be implanted on or within cranium 32, in some examples. As another example, leads 20 may be implanted within the same hemisphere of brain 28 or IMD 16 may be coupled to a single lead. In other examples, IMD 16 may be coupled to a leadless stimulator. In still other examples, IMD 16 may comprise an implantable fluid delivery device coupled to a catheter, rather than a lead.

Although leads 20 are shown in FIG. 1 as being coupled to a common lead extension 18, in other examples, leads 20 may be coupled to IMD 16 via separate lead extensions or directly to connector 30. Leads 20 may be positioned to deliver electrical stimulation to one or more target tissue sites (also referred to herein as "therapy targets") within brain 28 to manage patient symptoms associated with a patient condition, such as a movement disorder. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. For example, electrodes 24, 26 may be surgically implanted under the dura mater of brain 28 or within the cerebral cortex of brain 28 via a burr hole in cranium 32 of patient 12, and electrically coupled to IMD 16 via one or more leads 20.

In the example shown in FIG. 1, electrodes 24, 26 of leads 20 are shown as ring electrodes. Ring electrodes may be used in DBS applications because they are relatively simple to program and are capable of delivering an electrical field to any tissue adjacent to electrodes 24, 26. In other examples, electrodes 24, 26 may have different configurations. For example, in some examples, at least some of the electrodes 24, 26 of leads 20 may have a complex electrode array geometry that is capable of producing shaped electrical fields. The complex electrode array geometry may include multiple electrodes (e.g., partial ring or segmented electrodes) around the outer perimeter of each lead 20, rather than one ring electrode. In this manner, electrical stimulation may be directed in a specific direction from leads 20 to enhance therapy efficacy and reduce possible adverse side effects from stimulating a large volume of tissue.

An example of a complex electrode array geometry including segmented electrodes is shown and described with reference to FIGS. 3A and 3B. In some examples, a housing of IMD 16 may include one or more stimulation and/or sensing electrodes. In alternative examples, leads 20 may have shapes other than elongated cylinders as shown in FIG. 1. For example, leads 20 may be paddle leads, spherical leads, bendable leads, or any other type of shape effective in treating patient 12 and/or minimizing invasiveness of leads 20. In addition, in other examples, leads 20 may include both macro electrodes (e.g., rings, segments adapted to sensing local field potentials and stimulation) and micro electrodes (e.g., adapted to sensing spike trains in the time domain) in any combination.

In the example shown in FIG. 1, IMD 16 includes a memory (shown in FIG. 4) to store a plurality of therapy programs that each define a set of therapy parameter values. In some examples, IMD 16 may select a therapy program from the memory based on various parameters, such as a detected patient activity level, a detected patient state, based on the time of day, and the like. IMD 16 may generate electrical stimulation based on the selected therapy program to manage the patient symptoms associated with a movement disorder (or another patient condition). In accordance with the techniques of this disclosure, the memory of IMD 16 may store graphics processing data that may be applied during a rendering process to produce an image of an anatomical feature, such as brain 28, of patient 12. A computing device, such as programmer 14, may retrieve the graphical processing data, e.g., via wireless telemetry, to perform the rendering process using the graphical processing data.

During a trial stage in which IMD 16 is evaluated to determine whether IMD 16 provides efficacious therapy to patient 12, a plurality of therapy programs may be tested and evaluated for efficacy. In addition, one or more stimulation electrode combinations may be selected for the one or more therapy programs based on at least one sensed bioelectrical brain signal and a physiological model that is determined based on a location of leads 20 within brain 28, as described in further detail below. Therapy programs may be selected for storage within IMD 16 based on the results of the trial stage.

During chronic therapy in which IMD 16 is implanted within patient 12 for delivery of therapy on a non-temporary basis, IMD 16 may generate and deliver stimulation signals to patient 12 according to different therapy programs. In addition, in some examples, patient 12 may modify the value of one or more therapy parameter values within a single given program or switch between programs in order to alter the efficacy of the therapy as perceived by patient 12 with the aid of programmer 14. The memory of IMD 16 may store instructions defining the extent to which patient 12 may adjust therapy parameters, switch between programs, or undertake other therapy adjustments. Patient 12 may generate additional programs for use by IMD 16 via external programmer 14 at any time during therapy or as designated by the clinician.

External programmer 14 wirelessly communicates with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 16. Moreover, a clinician programmer may be configured to perform a rendering process using the graphics processing data stored on IMD 16, whereas a patient programmer is typically not (though may be) configured to perform the rendering process.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., activation of power, or the buttons and the keypad may be soft keys that change in function depending upon the section of the user interface currently viewed by the user. Alternatively, the screen (not shown) of programmer 14 may be a touchscreen that allows the user to provide input directly to the user interface shown on the display. The user may use a stylus or a finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a medical device programmer 14. A wireless adapter coupled to the computing device may enable secure communication between the computing device and IMD 16. Elements of the programmer may also be implemented using networked computing resources such that significant computation occurs remotely.

When programmer 14 is configured for use by the clinician, programmer 14 may be used to transmit initial programming information to IMD 16. This initial information may include hardware information, such as the type of leads 20 and the electrode arrangement, the position of leads 20 within brain 28, the configuration of electrode array 24, 26, initial programs defining therapy parameter values, and any other information the clinician desires to program into IMD 16. Programmer 14 may also be capable of completing functional tests (e.g., measuring the impedance of electrodes 24, 26 of leads 20).

The clinician may also store therapy programs within IMD 16 with the aid of programmer 14. During a programming session, the clinician may determine one or more therapy programs that provide efficacious therapy to patient 12 to address symptoms associated with the patient condition, and, in some cases, specific to one or more different patient states, such as a sleep state, movement state or rest state. For example, the clinician may select one or more stimulation electrode combinations with which stimulation is delivered to brain 28. During the programming session, patient 12 may provide feedback to the clinician as to the efficacy of the specific program being evaluated or the clinician may evaluate the efficacy based on one or more physiological parameters of patient 12 (e.g., muscle activity or muscle tone). Programmer 14 may assist the clinician in the creation/identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Programmer 14 may also provide an indication to patient 12 when therapy is being delivered, when patient input has triggered a change in therapy or when the power source within programmer 14 or IMD 16 needs to be replaced or recharged. For example, programmer 14 may include an alert LED, may flash a message to patient 12 via a programmer display, generate an audible sound or somatosensory cue to confirm patient input was received, e.g., to indicate a patient state or to manually modify a therapy parameter.

Programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the IEEE 802.11 or Bluetooth® specification sets, infrared (IR) communication according to the IRDA specification set, or other standard or proprietary telemetry protocols. Programmer 14 may also communicate with other programming or computing devices via exchange of removable media, such as magnetic or optical disks, or memory cards. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 can be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads, implanted leads via a percutaneous extension or one or more external leads. If the trial stimulator indicates DBS system 10 provides effective treatment to patient 12, the clinician may implant a chronic stimulator within patient 12 for relatively long-term treatment.

In other examples of therapy system 10, therapy system 10 includes only one lead or more than two leads. The devices, systems, and techniques described below can be applied to a therapy system that includes only one lead or more than two leads. Likewise, the techniques of this disclosure may be applied to other implantable medical devices, such as implantable fluid delivery devices that deliver a fluid-based medication to a therapy target of patient 12 via, e.g., a catheter.

Figure 2:
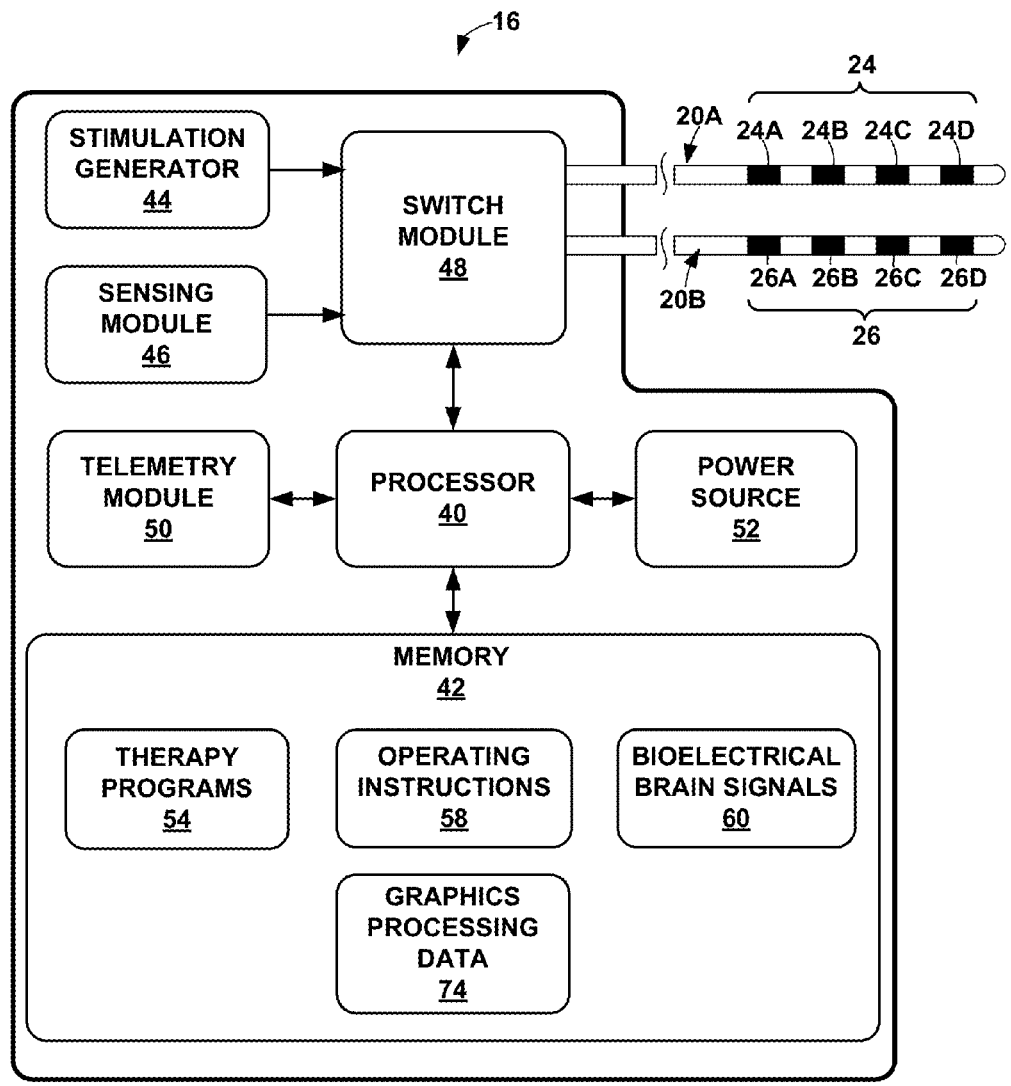
FIG. 2 is a functional block diagram illustrating components of an example implantable medical device (IMD).

FIG. 2 is a functional block diagram illustrating components of an example IMD 16. In the example shown in FIG. 2, IMD 16 includes processor 40, memory 42, electrical stimulation generator 44, sensing module 46, switch module 48, telemetry module 50, and power source 52. Memory 42 may include any volatile or non-volatile media, such as a random access memory (RAM), read only memory (ROM), non-volatile RAM (NVRAM), electrically erasable programmable ROM (EEPROM), flash memory, and the like. Memory 42 may store computer-readable instructions that, when executed by processor 40, cause IMD 16 to perform various functions.

In the example shown in FIG. 2, memory 42 stores therapy programs 54, bioelectrical brain signals 60, operating instructions 58, and graphics processing data 74 within memory 42 or separate areas within memory 42. In some examples, memory 42 represents separate memories for individually storing therapy programs 54, bioelectrical brain signals 60, operating instructions 58, and graphics processing data 74. Each stored therapy program 54 defines a particular set of electrical stimulation parameters, such as a stimulation electrode combination, current or voltage amplitude, frequency (e.g., pulse rate in the case of stimulation pulses), and pulse width.

In other examples, e.g., when IMD 16 comprises an implantable fluid delivery device, therapy programs 54 store instructions for fluid delivery dosing programs, e.g., a rate at which to deliver fluid and/or a time at which to deliver fluid at that rate, possibly including multiple rates scheduled out over a longer duration of days or weeks. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Bioelectrical brain signals 60 include bioelectrical brain signals sensed within brain 28 of patient 12 by sensing module 46. Example bioelectrical brain signals include, but are not limited to, a signal generated from local field potentials within one or more regions of brain 28. EEG and ECoG signals are examples of local field potentials that may be measured within brain 28. However, local field potentials may include a broader genus of electrical signals within brain 28 of patient 12. In some examples, bioelectrical brain signals 60 are raw bioelectrical brain signals sensed by sensing module 46 (or another sensing module), a parameterized bioelectrical brain signal generated by sensing module 46 or data generated based on the raw bioelectrical brain signal. Operating instructions 58 guide general operation of IMD 16 under control of processor 40.

In accordance with the techniques of this disclosure, memory 42 may store graphics processing data 74. In some examples, graphics processing data 74 may comprise a list of vertices for graphics primitives making up one or more graphics objects for a patient-specific model of an anatomical feature of patient 12. In some examples, graphics processing data 74 may comprise one or more transforms that can be applied to an anatomical atlas, which may comprise a general model of the anatomical feature of patient 12.

The anatomical feature of patient 12 represented by graphics processing data 74 may include a therapy target, at which leads 20 are implanted. Processor 40 need not interact with graphics processing data 74, other than to receive graphics processing data via telemetry module 50 and store the graphics processing data to memory 42. For example, processor 40 need not implement graphical rendering processes. In this manner, IMD 16 represents an example of a device that is not configured to perform a rendering process and that is associated with delivery of therapy to patient 12.

Processor 40 may include any one or more of a microprocessor, a controller, a digital signal processor (DSP), an application specific integrated circuit (ASIC), a field-programmable gate array (FPGA), or discrete logic circuitry. The functions attributed to processors described herein may be embodied in a hardware device via software, firmware, hardware or any combination thereof. Processor 40 controls stimulation generator 44 according to therapy programs 54 stored in memory 42 to apply particular stimulation parameter values specified by one or more of programs, such as amplitude, pulse width, and pulse rate. Processor 40 may control stimulation generator 44, sensing module 46, and switch module 48, among other elements of IMD 16, to deliver therapy to patient 12 via leads 20. Accordingly, portions of IMD 16, e.g., processor 40, stimulation generator 44, sensing module 46, and switch module 48, may collectively be referred to as a therapy unit of IMD 16.

In the example shown in FIG. 2, the set of electrodes 24 includes electrodes 24A, 24B, 24C, and 24D, and the set of electrodes 26 includes electrodes 26A, 26B, 26C, and 26D. Processor 40 also controls switch module 48 to apply the stimulation signals generated by stimulation generator 44 to selected combinations of electrodes 24, 26. In particular, switch module 48 may couple stimulation signals to selected conductors within leads 20, which, in turn, deliver the stimulation signals across selected electrodes 24, 26. Switch module 48 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 44 is coupled to electrodes 24, 26 via switch module 48 and conductors within leads 20. In some examples, however, IMD 16 does not include switch module 48 and instead contains a separate stimulation generator for each electrode.

Stimulation generator 44 can be a single channel or multi-channel stimulation generator. In particular, stimulation generator 44 may be capable of delivering a single stimulation pulse, multiple stimulation pulses, or a continuous signal at a given time via a single electrode combination or multiple stimulation pulses at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

In some examples, processor 40 dynamically changes the selected combinations of electrodes 24, 26, i.e., the stimulation electrode combination, based on one or more time or frequency domain characteristics of bioelectrical signals sensed within brain 28. Sensing module 46, under the control of processor 40, may sense bioelectrical brain signals and provide the sensed bioelectrical brain signals to processor 40. Processor 40 may control switch module 48 to couple sensing module 46 to a selected combinations of electrodes 24, 26, e.g., a sense electrode combination. In this way, IMD 16 is configured such that sensing module 46 may sense bioelectrical brain signals with a plurality of different sense electrode combinations. Switch module 48 may be electrically coupled to the selected electrodes 24, 26 via the conductors within the respective leads 20, which, in turn, deliver the bioelectrical brain signal sensed across the selected electrodes 24, 26 to sensing module 46. The bioelectrical brain signal may include electrical signals that are indicative of electrical activity within brain 28 of patient 12. Processor 40 can store the sensed bioelectrical brain signals in memory 42.

Although sensing module 46 is incorporated into a common housing with stimulation generator 44 and processor 40 in FIG. 2, in other examples, sensing module 46 may be in a separate housing from IMD 16 and may communicate with processor 40 (and, in some examples, programmer 14) via wired or wireless communication techniques.

Telemetry module 50 supports wireless communication between IMD 16 and an external programmer 14 or another computing device under the control of processor 40. Processor 40 of IMD 16 may receive, as updates to programs, values for various stimulation parameters such as amplitude and electrode combination, from programmer 14 via telemetry module 50. The updates to the therapy programs may be stored within therapy programs 54 portion of memory 42. Telemetry module 50 in IMD 16, as well as telemetry modules in other devices and systems described herein, such as programmer 14, may accomplish communication by RF communication techniques. In addition, telemetry module 50 may communicate with external medical device programmer 14 via proximal inductive interaction of IMD 16 with programmer 14. Accordingly, telemetry module 50 may send information, such as information relating to sensed bioelectrical brain signals, to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Throughout the disclosure, a group of electrodes may refer to any electrodes located at the same position along the longitudinal axis of one or more leads. A group of electrodes may include one electrode or a plurality of electrodes (e.g., two or more electrodes).

In this manner, FIG. 2 represents an example of an implantable medical device including a memory configured to store data for a program of the implantable medical device, a therapy unit configured to deliver a therapy to a therapy target of an anatomical feature of a patient, and an interface configured to receive the data for the program and to store the data for the program to the memory, wherein the interface is further configured to receive graphics processing data comprising data that, when applied during a rendering process, produces an image of the anatomical feature of the patient, wherein the implantable medical device is not configured to perform the rendering process using the graphics processing data. FIG. 2 also represents an example of an implantable medical device that includes a therapy unit configured to perform at least one of delivery of a therapy and measurement of physiologic signals at a therapy target of an anatomical feature of a patient, and a memory comprising stored data for a program of the implantable medical device and graphics processing data, wherein the graphics processing data comprises data that, when applied during a rendering process, produces an image of the anatomical feature of the patient, wherein the implantable medical device is not configured to perform the rendering process using the graphics processing data.

Figure 3A:
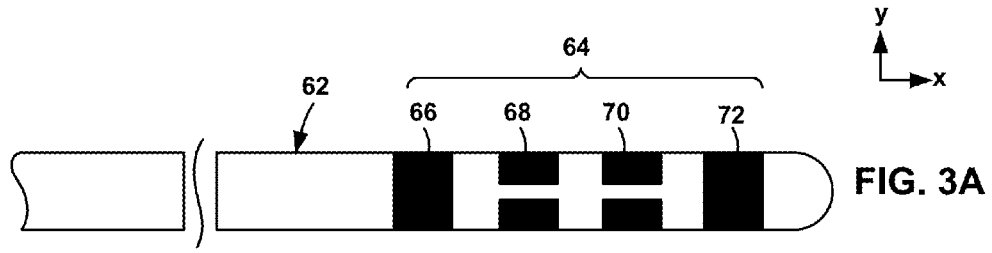
FIGS. 3A and 3B are schematic illustrations of an example lead and groups of electrodes that may be used with an IMD.
Figure 3B:
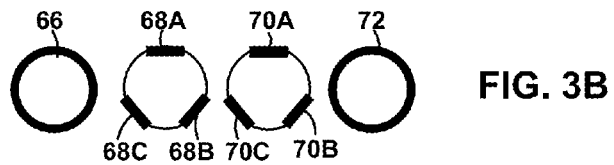

FIGS. 3A and 3B are schematic illustrations of an example lead 62 and groups of electrodes 64 that may be used with IMD 16 instead of or in addition to one or both leads 20A, 20B including respective sets of electrodes 24, 26. FIG. 3A shows a two-dimensional (2D) side view in the x-y plane (orthogonal x-y axes are shown in FIG. 3A for ease of description only) of lead 62, which includes four groups of electrodes 66, 68, 70, and 72. FIG. 3B shows a cross-sectional view in the y-z plane of each of the four groups of electrodes. Groups of electrodes 66 and 72 each comprise one ring electrode, which may be similar to each of electrodes 24, 26 shown in FIG. 2. In contrast, groups of electrodes 68 and 70 each comprise three segmented electrodes 68A-68C and 70A-70C distributed around the outer perimeter of lead 62. In other examples, lead 62 may comprise any number and combination of groups of ring electrodes or segmented electrodes. For example, lead 62 may comprise only groups of segmented electrodes. As another example, groups 68, 70 of electrodes may comprise more than three segmented (or partial ring) electrodes or one or two segmented or partial ring electrodes.

In accordance with the techniques of this disclosure, in some examples, graphics processing data stored to IMD 16 and/or programmer 14 may include data representative of the location of lead 62 implanted within a therapy target of patient 12. For example, IMD 16 may store information defining the location of lead 62 in the form of a point representative of the distal tip of lead 62 and an angle of lead 62 relative to the distal tip. It may also store information about the axial rotation of a lead or catheter relative to anatomical midline (or another reference), so as to be able to render the directionality of relevant therapy elements correctly (e.g. the orientation of a egress hole in a catheter tip). In other examples, IMD 16 may store information defining locations of centers of electrodes 66, 68, 70, 72. In such examples, IMD 16 may further store information indicating types for electrodes 66, 68, 70, 72, e.g., to indicate that electrodes 66, 72 comprise ring electrodes, whereas electrodes 68A-68C and 70A-70C comprise segmented electrodes. IMD 16 may further store information indicating locations of segments of segmented electrodes 68A-68C and 70A-7C.

Figure 3C:
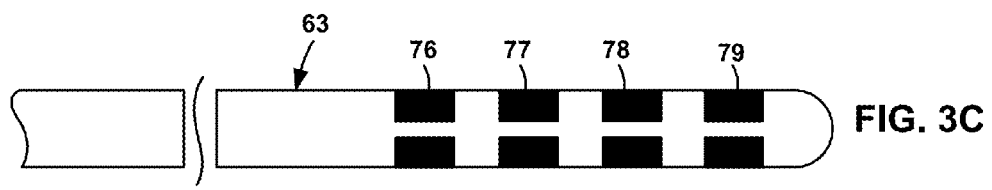
FIG. 3C is a schematic illustration of another example lead and electrodes that may be used with an IMD.

FIG. 3C is a schematic illustration of an example lead 63 and electrodes 76-79. Lead 63 conforms substantially to lead 62 of FIGS. 3A and 3B. However, in this example, electrodes 76-79 of lead 63 are all segmented. In this manner, lead 63 represents an example of a fully segmented lead having four levels of segmented electrodes. Electrodes 76-79 may have, e.g., three or four segments, in various examples. Lead 63 represents another example of a therapy element to which an IMD, such as IMD 16, may be coupled. IMD 16 may be coupled to two or more leads similar to lead 63. In other examples, a fully segmented lead may have more or fewer electrodes.

Figure 4:
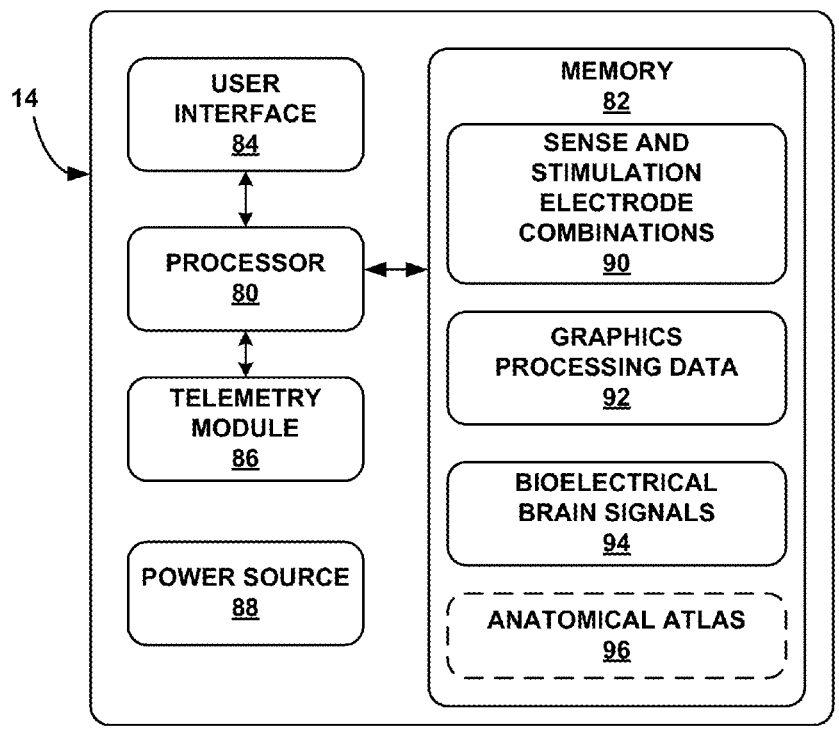
FIG. 4 is a conceptual block diagram of an example external medical device programmer.

FIG. 4 is a conceptual block diagram of an example external medical device programmer 14, which includes processor 80, memory 82, user interface 84, telemetry module 86, and power source 88. Processor 80 controls user interface 84 and telemetry module 86, and stores and retrieves information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80.

A user, such as a clinician or patient 12, may interact with programmer 14 through user interface 84. Accordingly, in some examples, programmer 14 may comprise a patient programmer or a clinician programmer. The techniques of this disclosure are directed to storing graphics processing data, such as graphics processing data 92, to a device associated with delivering therapy to a therapy target of a patient, while not being configured to perform a rendering process using the graphics processing data. Accordingly, when programmer 14 is configured as a patient programmer, in some examples, the patient programmer is not necessarily configured to perform the rendering process using graphics processing data 92. In some examples, when programmer 14 is configured as a clinician programmer, processor 80 may be configured to perform the rendering process using graphics processing data 92 to generate an image of an anatomical feature including the therapy target of patient 12, and to display the image, e.g., via user interface 84.

User interface 84 includes a display (not shown), such as a LCD or LED display or other type of screen, to present information related to the therapy, such as information related to bioelectrical signals sensed via a plurality of sense electrode combinations and in some examples, when configured to render graphics objects, an image of an anatomical feature including a therapy target of patient 12. In addition, user interface 84 may include an input mechanism to receive input from the user. The input mechanisms may include, for example, buttons, a keypad (e.g., an alphanumeric keypad), a peripheral pointing device, or another input mechanism that allows the user to navigate through user interfaces presented by processor 80 of programmer 14 and provide input.

If programmer 14 includes buttons and a keypad, the buttons may be dedicated to performing a certain function, e.g., a power button, or the buttons and the keypad may be soft keys that change in function depending upon the section of the user interface currently viewed by the user. Alternatively, the display (not shown) of programmer 14 may be a touch screen that allows the user to provide input directly to the user interface shown on the display. The user may use a stylus or a finger to provide input to the display. In other examples, user interface 84 also includes audio circuitry for providing audible instructions or sounds to patient 12 and/or receiving voice commands from patient 12, which may be useful if patient 12 has limited motor functions. Patient 12, a clinician or another user may also interact with programmer 14 to manually select therapy programs, generate new therapy programs, modify therapy programs through individual or global adjustments, and transmit the new programs to IMD 16.

In some examples, at least some of the control of therapy delivery by IMD 16 may be implemented by processor 80 of programmer 14. In addition, in some examples, processor 80 may select a stimulation electrode combination based on a bioelectrical brain signal sensed by IMD 16 and a physiological model that indicates a one or more characteristics of tissue of brain 28 of patient 12 proximate implanted electrodes 24, 26 of leads 20. The examples described herein primarily refer to a bioelectrical brain signal sensed by IMD 16, but are also applicable to selecting an electrode combination based on a bioelectrical brain signal sensed by a sensing module that is separate from IMD 16. The separate sensing module may, but need not be, implanted within patient 12.

In some examples, a clinician or other user of programmer 14 may select one or more electrodes based on time domain characteristics of a sensed bioelectrical signal, such as a sensed spike train from an individual or small group of neurons. In addition, the user may view an image of an anatomical feature of patient 12, which may include a representation of implanted therapy elements of IMD 16, to select the electrodes. In some cases, e.g., after determining a desirable stimulation electrode combination, processor 80 may transmit a signal to IMD 16 to instruct IMD 16 to use the selected stimulation electrode combinations.

Processor 40 of IMD 16 may receive the signal from programmer 14 via its respective telemetry module 50 (FIG. 2). Processor 40 of IMD 16 may switch stimulation electrode combinations by selecting a stored therapy program from memory 42 based on the signal from processor 80 of programmer 14. Alternatively, processor 80 of programmer 14 may select a therapy program or a specific stimulation electrode combination and transmit a signal to IMD 16, where the signal indicates the therapy parameter values to be implemented by IMD 16 to help improve the efficacy of the stimulation to manage the patient's movement disorder. The indication may be, for example, an alphanumeric identifier or symbol that is associated with the therapy program in memory 42 of IMD 16.

In the example shown in FIG. 4, memory 82 stores sense and stimulation electrode combinations 90, graphics processing data 92, bioelectrical brain signals 94, and anatomical atlas 96 in separate memories within memory 82 or separate areas within memory 82. Memory 82 may also include instructions for operating user interface 84 and telemetry module 86, and for managing power source 88. Memory 82 may also store any therapy data retrieved from IMD 16 during the course of therapy, such as bioelectrical brain signals 94 sensed by IMD 16. The clinician may use this therapy data to determine the progression of the patient condition in order to predict future treatment. Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Sense and stimulation electrode combinations 90 stores sense electrode combinations and associated stimulation electrode combinations. As described above, in some examples, the sense and stimulation electrode combinations may include the same subset of electrodes 24, 26, or may include different subsets of electrodes. Thus, memory 82 can store a plurality of sense electrode combinations and, for each sense electrode combination, store information identifying the stimulation electrode combination that is associated with the respective sense electrode combination. The associations between sense and stimulation electrode combinations can be determined, e.g., by a clinician, automatically by processor 80, or a processor of another device (e.g., IMD 16).

In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy. In some examples, as discussed above, stimulation may be delivered via a stimulation electrode combination to a tissue site that is different than the tissue site closest to the corresponding sense electrode combination but is within the same region, e.g., the thalamus, of brain 28 in order to mitigate any irregular oscillations or other irregular brain activity within the tissue site associated with the sense electrode combination. In another example, stimulation may be delivered via a stimulation electrode combination to a tissue site that is different than the tissue site closest to the corresponding sense electrode combination but is within the same pathway or brain circuit, e.g., IMD 16 may sense bioelectrical brain signals in the GPi and stimulate in the STN of brain 28 in order to mitigate any abnormal oscillatory activity or other abnormal brain activity within the tissue site associated within the sense electrode combination. The regions of the brain circuit may be functionally related to one another via neurological pathways in a manner that causes activity within one region of the network to be influenced by activity within another region of the network.

Graphics processing data 92 stores information with which processor 80 of programmer 14 may, when configured to perform a rendering process, render a patient-specific model to generate an image of a therapy target proximate leads 20 of IMD 16. In some examples, the image may include one or more anatomical structures within brain 28 of patient 12 proximate implanted leads 20. In some examples, graphics processing data 92 stores lead placement information that identifies a location of leads 20, which can be an actual location of leads 20 within brain 28 or an approximate location of leads 20 within brain 28. The information relating to the actual or approximate location of leads 20 can include, for example, points representing distal tips of the leads, angles of the leads relative to the distal tips, a three-dimensional vector relative to the distal tip, second point representative of a proximal ends of the leads, points defining centroids of electrodes along a lead, axial orientation or rotation relative to a reference direction, or other such information.

Graphics processing data 92 also stores data that, when applied during a rendering process, produces an image representative of an anatomical feature of patient 12 including a therapy target proximate to leads 20 of IMD 16. In one example, graphics processing data 92 may store a list of vertices defining graphics primitives for a three-dimensional mesh representative of the patient-specific model of the anatomical feature. In this example, memory 82 need not necessarily store anatomical atlas 96, which is illustrated using a dashed outline to represent that storing data for anatomical atlas 96 is optional. In another example, graphics processing data 92 may store one or more transforms that, when applied to anatomical atlas 96, transform anatomical atlas 96 to the patient-specific model. Such a transform may be generated by a process in which a non-patient specific atlas or data set is altered via a series of rigid or non-rigid registrations such that it better matches this patient's specific anatomy. The rendering process may further include generating pixel data for an image of the anatomical feature from the patient-specific model. In some examples, graphics processing data 92 may store both vertex data and transform data, which may both be applied during the rendering process. In still other examples, memory 82 may additionally store image data, e.g., an encoded representation of a portion of the image to be displayed.

When programmer 14 is configured as a clinician programmer, memory 82 may store graphics processing data 92 temporarily. That is, the clinician programmer may retrieve graphics processing data 74 from memory 42 of IMD 16, e.g., via wireless telemetry, and store the graphics processing data temporarily as graphics processing data 92. In other examples, the clinician programmer may retrieve graphics processing data from a patient programmer and store the retrieved graphics processing data as graphics processing data 92. The clinician programmer may store graphics processing data 92 during a programming session performed by a clinician user, and processor 80 (or a separate processor, such as a graphics processing unit (GPU)), may be configured to perform the rendering process. Following the programming session, processor 80 may erase graphics processing data 92 or overwrite graphics processing data 92 when new data is to be stored to memory 82. Graphics processing data may alternately be stored locally or cached for future use on this programmer. Processor 80 may cause a display (not shown) of user interface 84 to display an image generated by performance of the rendering process.

Wireless telemetry in programmer 14 may be accomplished by RF communication or proximal inductive interaction of external programmer 14 with IMD 16. This wireless communication is possible through the use of telemetry module 86. Accordingly, telemetry module 86 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 88 delivers operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate. Power source 88 may include circuitry to monitor power remaining within a battery. In this manner, user interface 84 may provide a current battery level indicator or low battery level indicator when the battery needs to be replaced or recharged. In some cases, power source 88 may be capable of estimating the remaining time of operation using the current battery.

Figure 5:
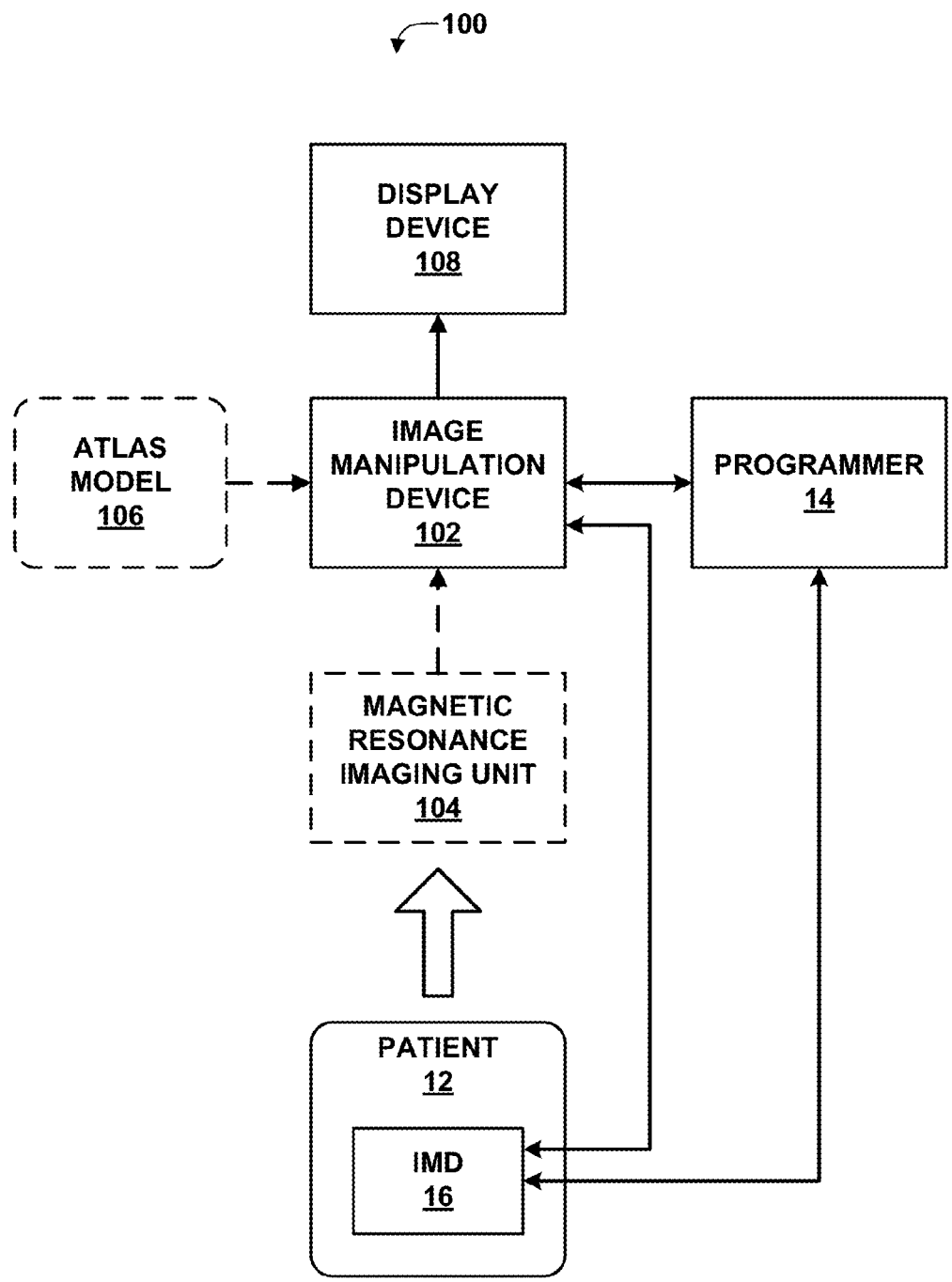
FIG. 5 is a block diagram illustrating an example system in which an image manipulation device stores graphics processing data to devices associated with delivering therapy to a patient.

FIG. 5 is a block diagram illustrating an example system 100 in which an image manipulation device 102 stores graphics processing data to devices associated with delivering therapy to patient 12. In the example of FIG. 5, system 100 includes image manipulation device 102, display device 108, magnetic resonance imaging (MRI) unit 104, atlas model 106, programmer 14, and IMD 16 implanted with patient 12. For the purposes of the example of FIG. 5, it is assumed that programmer 14 comprises a patient programmer for patient 12 that is not configured to perform a graphics rendering process. However, as discussed above, in other examples, programmer 14 may comprise a clinician programmer or other programmer device configured to perform the rendering process. Moreover, in some examples, image manipulation device 102 and a clinician programmer may be functionally integrated as one device or one unit.

MRI unit 104 may capture a series of magnetic resonance images of an anatomical feature including a therapy target of patient 12 while IMD 16 is implanted within patient 12. Accordingly, a therapy element of IMD 16, such as one or more leads or one or more catheters, may be implanted proximate to the therapy target. Although the example of FIG. 5 depicts an MRI unit, in other examples, other imaging devices may be used, e.g., CT units, x-ray units, fluoroscopy units, and the like. MRI unit 104 may capture a series of images of the anatomical feature of patient 12, which may include images of the therapy element of IMD 16. In some examples, MRI unit 104 may capture a set of images of the therapy target of patient 12 prior to implant of the therapy element and IMD 16, in order to assist physicians in planning placement of the therapy element of IMD 16. In some examples, MRI unit 104 may capture a set of images following implant, e.g., to assist clinicians in programming of IMD 16.

MRI unit 104 provides the captured images to image manipulation device 102. Image manipulation device 102 may use the images from MRI unit 104 to construct a patient-specific model of the anatomical feature including the therapy target of patient 12. As an example, the MRI image data may be used to alter a non-patient specific atlas or data set a series of rigid or non-rigid registrations such that it better matches this patient's specific anatomy. The patient-specific model may correspond to a three-dimensional model of the anatomical feature specific to patient 12. For example, the patient-specific model may comprise one or more graphics objects made up of one or more graphics primitives. Each of the graphics primitives may be defined by one or more vertices. In some examples, certain portions of the anatomical feature of patient 12 may be pre-stored to image manipulation device 102, and graphics processing data for producing an image of patient-specific structures of interest may be stored to IMD 16 and/or programmer 14, e.g., the therapy target and neighboring structures.

In accordance with the techniques of this disclosure, in some examples, image manipulation device 102 may be configured to store a list of vertices defining the graphics primitives for the graphics objects making up the patient-specific model to a device that is not configured to perform a rendering process but that is associated with delivering therapy to patient 12, e.g., programmer 14 and/or IMD 16, in this example. In this manner, storing a list of vertices to programmer 14 or IMD 16 represents an example of storing graphics processing data to a device associated with delivering therapy to a patient. In such examples, image manipulation device 102 need not necessarily access data of atlas model 106. That is, the list of vertices can be used to directly recreate the patient-specific model. Therefore, atlas model 106 is illustrated using a dashed outline, indicating that atlas model 106 is an optional component of system 100. Atlas model 106 is generally ubiquitous, that is, available to any device configured to interact with graphics processing data stored by IMD 16 and/or programmer 14.

In other examples of the techniques of this disclosure, image manipulation device 102 may be configured to compare the patient-specific model to atlas model 106, e.g., to determine differences between the models. Image manipulation device 102 may be configured to calculate one or more transforms that, when applied to atlas model 106, produce a model that is substantially similar to the patient-specific model for patient 12. In these examples, image manipulation device 102 may store data for the transforms to programmer 14 and/or IMD 16. In this manner, storing transform data to programmer 14 or IMD 16 represents an example of storing graphics processing data to a device associated with delivering therapy to a patient.

Likewise, image manipulation device 102 may determine locations of therapy elements of IMD 16 within the anatomical feature of patient 12 from the images received from MRI unit 104. Image manipulation device 102 may store data indicative of the locations of therapy elements to IMD 16 or programmer 14, such as a point and one or more angles (which can be stored efficiently in tens of bytes), two points defining a line, multiple points corresponding to centers of electrodes of a lead, a point representative of a leadless stimulator, or other location data. The data indicative of the location of the therapy element may also include geometry information for the therapy element, such as, for example, a model identifier (e.g., model number) of the therapy element, a length and width (e.g., circumference) of the therapy element, a number of electrodes and positions of the electrodes (which may be described by spacing between the electrodes) when the therapy element comprises a lead, coefficients of a curve (spline or otherwise) when the therapy element is not straight, or other such information.

When graphics processing data are stored to programmer 14 and/or IMD 16, image manipulation device 102 may retrieve the graphics processing data from programmer 14 or IMD 16. In some examples, image manipulation device 102 may be configured only to perform a graphics rendering process, and not to generate an actual patient-specific model from data of MRI unit 104. Accordingly, MRI unit 104 is illustrated using a dashed line to indicate that MRI unit 104 is an optional component of system 100. In some examples, image manipulation device 102 may be configured to retrieve the graphics processing data from programmer 14 or IMD 16, as well as to produce a patient-specific model of the anatomical feature of patient 12, e.g., to assist a clinician in monitoring drift of leads of IMD 16, if any.

In this manner, image manipulation device 102 may have various configurations. For example, image manipulation device 102 may be configured to generate graphics processing data to be stored to IMD 16 and/or programmer 14, to retrieve graphics processing data from IMD 16 and/or programmer 14 and perform a rendering process using the graphics processing data, or both.

Display device 108 may comprise a user interface for displaying images rendered by image manipulation device 102. In some examples, display device 108 may form part of image manipulation device 102, or may comprise a separate device coupled to image manipulation device 102. Image manipulation device 102 may apply the graphics processing data during a rendering process to generate an image of an anatomical feature of patient 12 including a therapy target, and of therapy elements of IMD 16 in some examples. Image manipulation device 102 may cause display device 108 to display the image after rendering.

In this manner, FIG. 5 represents an example of a system including an implantable medical device comprising a memory that stores graphics processing data, wherein the implantable medical device is configured to at least one of deliver therapy and sense a physiological signal at a therapy target of a patient, and wherein the implantable medical device is not configured to perform a rendering process using the graphics processing data, and an image manipulation device configured to retrieve the graphics processing data from the memory of the implantable medical device, to apply the graphics processing data while performing the rendering process to generate an image of an anatomical feature of the patient, wherein the anatomical feature comprises the therapy target for the implantable medical device, and to cause a user interface of a display unit to display the image, wherein the image of the anatomical feature is specific to the patient.

The graphics processing data may be referred to as key information. In accordance with the techniques of this disclosure, this key information can be stored to a device associated with delivering therapy to patient 12, e.g., IMD 16 and/or programmer 14. In this manner, the key information can be retrieved, rather than regenerated, e.g., by obtaining a subsequent set of MRI images. The key information may include graphics processing data that, when applied during a rendering process, allows for a visualization programming interface to be presented. Because the key information is stored to IMD 16 and/or programmer 14, image manipulation device 102 (or other devices, e.g., clinician programmers) may have access to the graphics processing data when patient 12 is present.

Figure 6A:
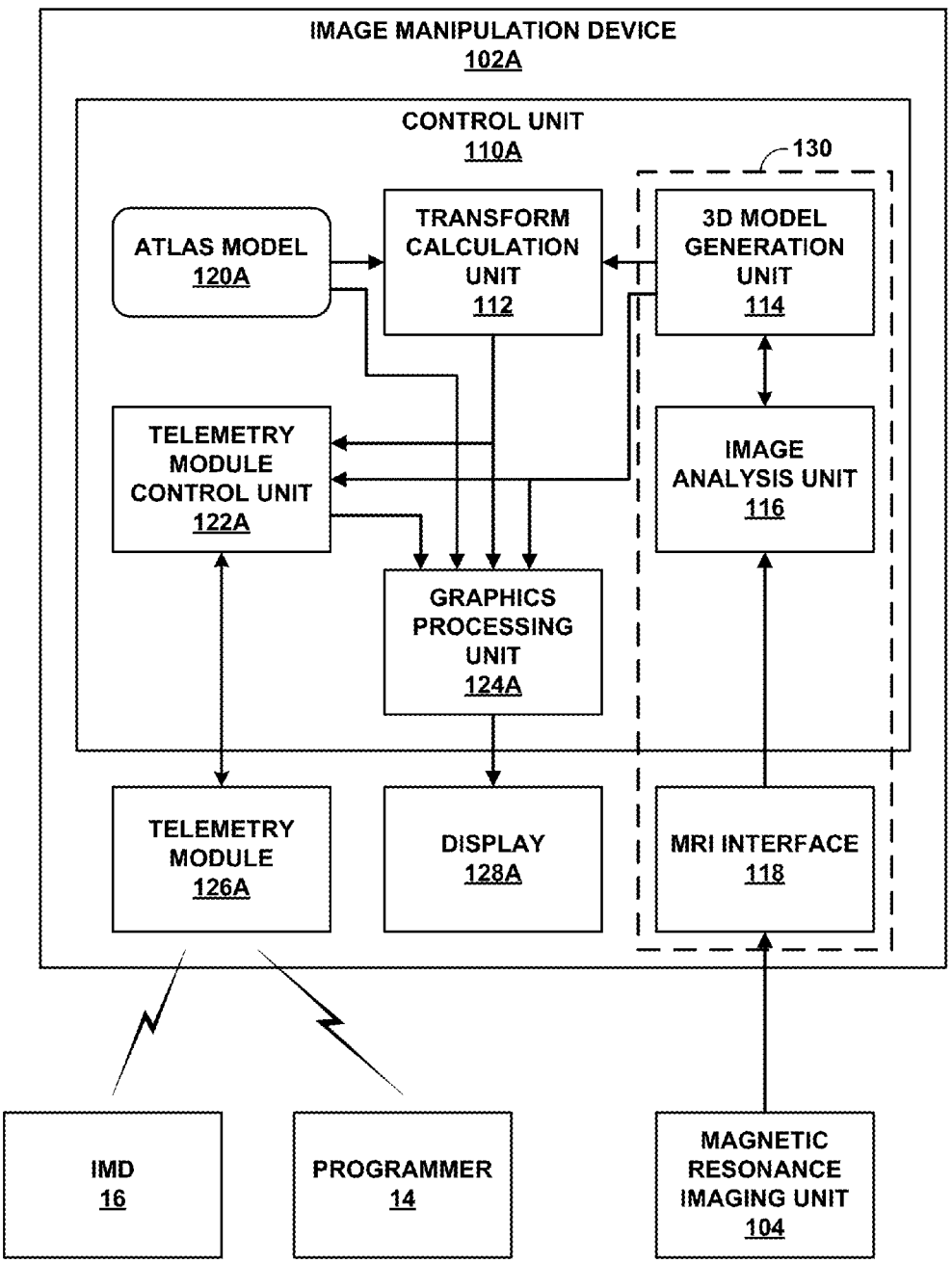
FIGS. 6A-6C are block diagrams illustrating various example configurations of components of image manipulation devices.
Figure 6B:
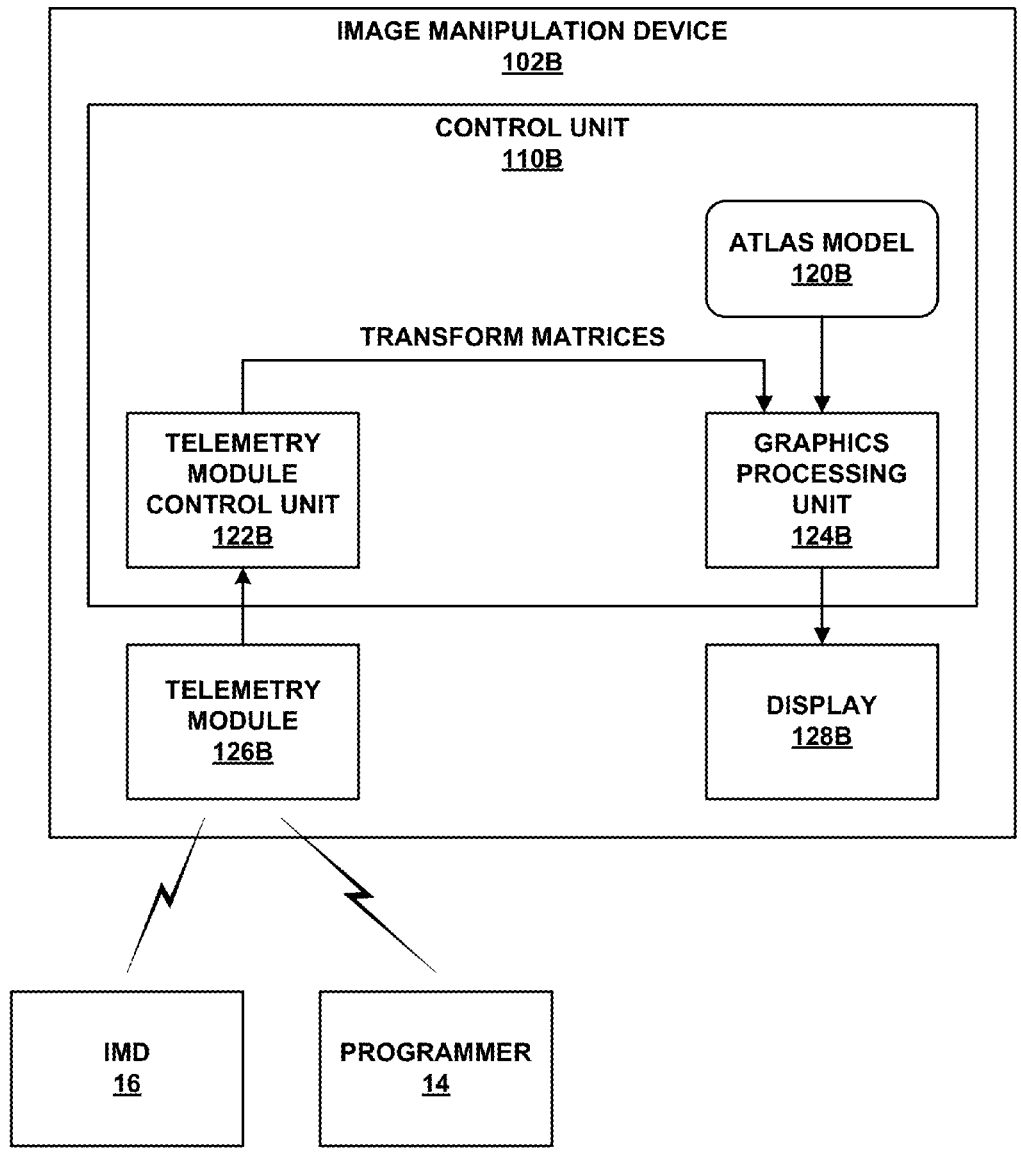
Figure 6C:
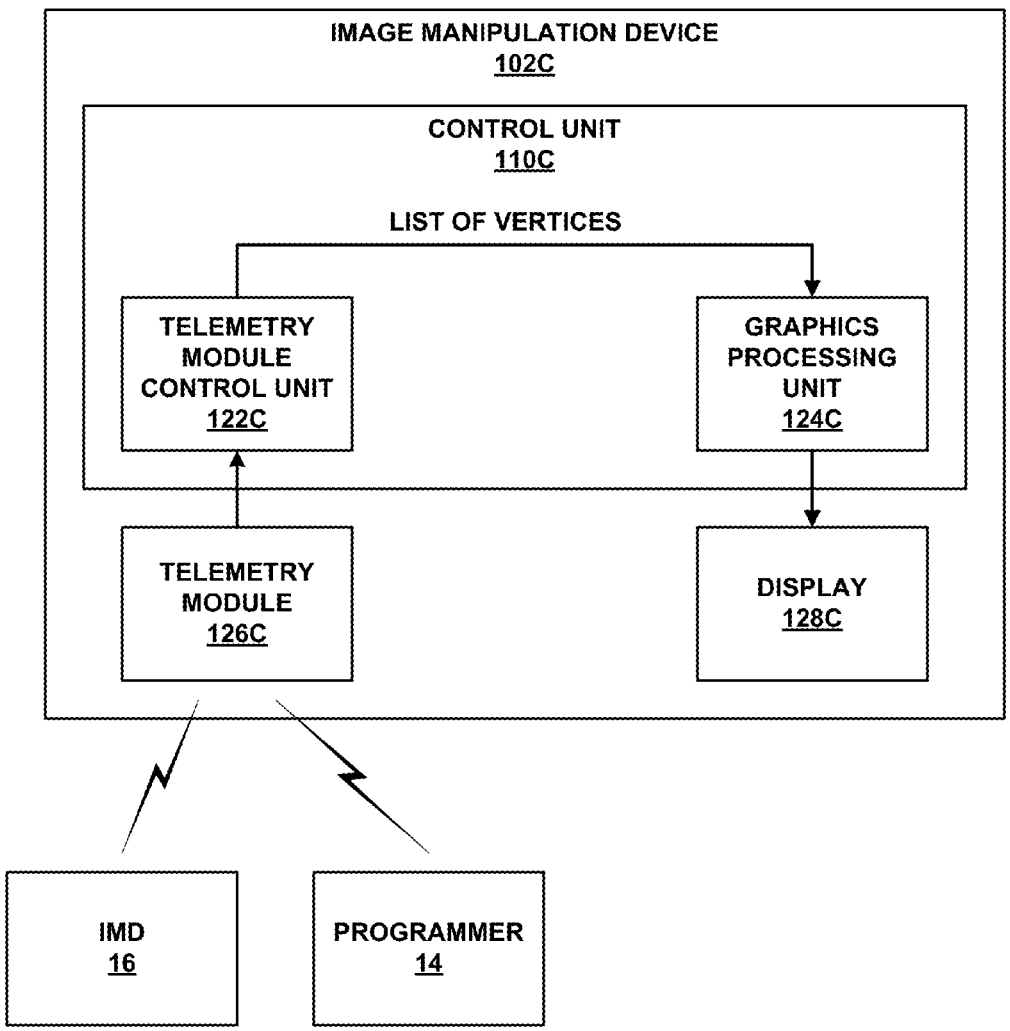

FIGS. 6A-6C are block diagrams illustrating various example configurations of components of image manipulation devices 102A-102C. Each of image manipulation devices 102A-102C conform substantially to various configurations of image manipulation device 102 of FIG. 5. In the example of FIG. 6A, image manipulation device 102A includes control unit 110A, telemetry module 126A, display 128A, and MRI interface 118.

Control unit 110A may include a memory for storing executable instructions and one or more processing units for executing the instructions. In other examples, control unit 110A may include one or more discrete hardware units, such as digital signal processors (DSPs), application specific integrated circuits (ASICs), field programmable gate arrays (FPGAs), or any other equivalent integrated or discrete logic circuitry. In the example of FIG. 6A, control unit 110A includes memory for storing atlas model 120A, as well as transform calculation unit 112, three-dimensional (3D) model generation unit 114, telemetry module control unit 122A, graphics processing unit 124A, and image analysis unit 116. In this example, 3D model generation unit 114, image analysis unit 116, and MRI interface 118 collectively form a patient-specific model generation unit 130. In other examples, patient-specific model generation unit 130 may correspond to a separate functional unit.

In the example of FIG. 6A, image manipulation device 102A receives images from MRI unit 104 via MRI interface 118. Image analysis unit 116 analyzes the images and provides data for the images to 3D model generation unit 114. 3D model generation unit 114 creates a patient-specific 3D model of an anatomical feature of patient 12 from the images received from MRI unit 104. The patient-specific model may comprise one or more graphics objects, each of which may comprise one or more graphics primitives. 3D model generation unit 114 may generate a list of vertices defining the graphics primitives and pass the list of vertices to telemetry module control unit 122A. Telemetry module control unit 122A may, in turn, cause telemetry module 126A to store the list of vertices to programmer 14 and/or IMD 16. In some examples, 3D model generation unit 114 may also provide other graphics processing data in addition to the list of vertices, such as arrangement of polygon faces among the vertices, to aid in reconstruction.

One common example of a graphics primitive is a triangle, which may be defined by three vertices in a three-dimensional space. That is, each of the vertices may comprise an X-component, a Y-component, and a Z-component. Thus, nine values may be used to define the geometry for a triangle graphics primitive. In some examples, an instruction to draw triangle graphics primitives may be followed by a list of X, Y, Z coordinate triplets, comprising a list of vertices. The instruction and list of vertices may case graphics processing unit (GPU) 124A to construct triangles having vertices starting with the first vertex, three vertices forming each of the triangles. Table 1 below provides an example of a list of vertices for rendering triangles.

TABLE 1

| X-Coordinate | Y-Coordinate | Z-Coordinate |
|---|---|---|
| 17.624 | 77.8872 | 42.9315 |
| 17.5931 | 78.2035 | 42.5784 |
| 21.9218 | 77.6171 | 42.1817 |
| 24.405 | 76.0362 | 49.9998 |
| 19.9519 | 78.3977 | 48.1534 |
| 24.2638 | 77.597 | 47.8474 |

In some examples, the first three rows of coordinates in Table 1 may define a first triangle, and the next three rows of Table 1 may define a second triangle. In other examples, rows 1 through 3 of Table 1 may define a first triangle, rows 2 through 4 may define a second triangle, rows 3 through 5 may define a third triangle, and so on. In this manner, a list of vertices, such as the list of vertices represented in Table 1, may define one or more graphics primitives that make up a graphics object for a patient-specific physiological model.

GPU 124A, or other GPUs of other image manipulation devices, may apply the list of vertices during a graphics rendering process to produce an image of the patient-specific model constructed by patient-specific model generation unit 130. For example, instructions may be passed to GPU 124A via an application programming interface (API), such as Open Graphics Library (OpenGL) DirectX, or other graphics processing APIs, to render the graphics objects defined by the list of vertices. The following pseudocode represents one example, using OpenGL-like syntax, for drawing triangles using the example list of vertices of Table 1:

glBegin(GL_TRIANGLES);
glVertex3f (17.624, 77.8872, 42.9315);
glVertex3f (17.5931, 78.2035, 42.5784);
glVertex3f (21.9218, 77.6171, 42.1817);
glVertex3f (24.405, 76.0362, 49.9998);
glVertex3f (19.9519, 78.3977, 48.1534);
glVertex3f (24.2638, 77.597, 47.8474);
glEnd( );

In this example pseudocode, glBegin(GL_TRIANGLES); is an instruction that causes GPU 124A to begin drawing triangles based on vertices passed to GPU 124A. Each of the glVertex3f( ) instructions correspond to instructions for passing vertices to GPU 124A to use to draw triangles, in the format glVertex3f(X, Y, Z). In this example, GPU 124A may draw two triangles, one triangle with the first three vertices and a second triangle with the next three vertices. The glEnd( ); instruction informs GPU 124A that the list has ended and to stop drawing triangles. In other examples, of course, there may be a much larger set of vertices (e.g., 1950 vertices) used to define many triangles (e.g., 650 triangles) to construct graphics objects for a patient-specific physiological model of an anatomical feature of patient 12. In some examples, 3D model generation unit 114A may define a vertex array to include the example list of vertices of Table 1. Thus, in some examples, image manipulation device 102A may store the vertex array to IMD 16 and/or programmer 14 via telemetry module 126A.

Rather than storing a list of vertices, in some examples, 3D model generation unit 114 sends the patient-specific model to transform calculation unit 112. Transform calculation unit 112 may also retrieve atlas model 120A from memory of control unit 110A. In this example, atlas model 120A corresponds to a general, non-patient-specific model of the anatomical feature of interest for patient 12. For example, atlas model 120A may be generated based on an average of patient-specific models of the anatomical feature from a relatively large number of test patients. Alternately, atlas model 120A may be generated from the dissection of a physical specimen wherein experts in the field segment structures based on staining or other techniques. As yet another example, atlas model 120A may be generated by statistical analysis of the correlation of therapy outcome against anatomical location using large sets of previous test patients.

Transform calculation unit 112 may calculate one or more transforms that, when applied to atlas model 120A, substantially yield the patient-specific model produced by patient-specific model generation unit 130. For example, a user may manipulate elements of the anatomical atlas model to move vertices or graphics objects of the atlas model to mirror the patient-specific model. In addition, or in the alternative, transform calculation unit 112 may match features of the patient-specific model to the atlas model and calculate the transforms to manipulate vertices of the atlas model to mirror the patient-specific model. The transforms may comprise any of translations, scaling, and/or rotations in one or more dimensions. Each of these types of transforms can be stored in, for example, a 3×3 matrix transform. In some examples, transform calculation unit 112 may calculate a 4×4 matrix comprising an affine transform that represents a combination of a translation transform, a scaling transform, and a rotation transform. Table 2 below represents an example 4×4 affine transform:

TABLE 2

| 1.000000 | 0.000000 | 0.000000 | 0.000000 |
|---|---|---|---|
| 0.000000 | 0.996265 | −0.062267 | 8.168664 |
| 0.000000 | 0.119729 | 0.996265 | −6.887179 |
| 0.000000 | 0.000000 | 0.000000 | 1.000000 |

In some examples, transform calculation unit 112 may be configured to operate completely autonomously to calculate the transforms. In other examples, a user may interact with transform calculation unit 112, e.g., to adjust the transforms to cause the model produced by applying the transforms to atlas model 120A to fit the patient-specific model more precisely. In still other examples, transform calculation unit 112 may represent a tool provided to a user to adjust atlas model 120A to substantially fit the patient-specific model, such that transform calculation unit 112 produces transforms corresponding to the adjustments made or to key landmarks identified by the user. In any case, transform calculation unit 112 may send the calculated transforms to telemetry module control unit 122A. Telemetry module control unit 122A may, in turn, cause telemetry module 126A to store the transforms to IMD 16 and/or programmer 14.

Moreover, transform calculation unit 112 may provide the transforms to GPU 124A. GPU 124A may also receive atlas model 120A. GPU 124A may perform a rendering process, during which GPU 124A may apply the transforms to atlas model 120A. In this manner, GPU 124A may manipulate vertices defining atlas model 120A according to the transforms from transform calculation unit 112 during a rendering process.

Accordingly, image manipulation device 102A represents an example of a device that can use graphics processing data comprising either or both of a list of vertices defining a patient-specific model and transforms applied to atlas model 120A (or in some cases, to the patient-specific model defined by the list of vertices). GPU 124A may apply the graphics processing data during a rendering process to produce an image of an anatomical feature of patient 12. GPU 124A may then pass the image to display 128A to cause a user interface of display 128A to display the image. In some examples, a clinician may use the image to adjust programming of IMD 16. In such examples, image manipulation device 102A may be configured as a clinician programmer.

Furthermore, rather than using the data provided by either or both of 3D model generation unit 114 and/or transform calculation unit 112, image manipulation device 102A may be configured to retrieve graphics processing data from IMD 16 and/or programmer 14 that was previously stored. Thus, GPU 124A may be configured to perform a rendering process using graphics processing data retrieved from IMD 16 and/or programmer 14, in addition to or in the alternative to graphics processing data constructed by patient-specific model generation unit 130 and/or transform calculation unit 112. For example, image manipulation device 102A may retrieve data from IMD 16 and/or programmer 14 rather than subjecting patient 12 to an additional imaging process using MRI unit 104 or other imaging devices, e.g., CT units, x-ray units, fluoroscopy units, or the like.

In still other examples, image manipulation device 102A may retrieve graphics processing data stored by IMD 16 and/or programmer 14 to produce a first image, and also generate an updated patient-specific model using patient-specific model generation unit 130 to produce a second image. In this manner, a clinician may compare the two images or compare to calculated transforms to determine whether therapy elements of IMD 16 have drifted over time.

In this manner, FIG. 6A represents an example of a device including a telemetry module configured to retrieve graphics processing data from a device that is not configured to perform a rendering process using the graphics processing data and that is associated with at least one of delivering therapy and sensing a physiological signal at a therapy target of a patient, and a control unit configured to apply the graphics processing data while performing the rendering process to generate an image of an anatomical feature of the patient, wherein the anatomical feature comprises the therapy target for an implantable medical device, and to cause a display unit of a user interface to display the image, wherein the image of the anatomical feature is specific to the patient.

FIG. 6B is a block diagram illustrating an example of image manipulation device 102B. Components of image manipulation device 102B that are named and numbered similarly to components of image manipulation device 102A of FIG. 6A conform substantially to the similarly named and numbered components. In this example, however, image manipulation device 102B does not include a patient-specific model generation unit. Furthermore, in this example, control unit 102B is configured to retrieve one or more transform matrices from IMD 16 and/or programmer 14 via telemetry module 126B. GPU 124B may apply the retrieved transform matrices to atlas model 102B during a rendering process to generate an image of an anatomical feature of patient 12 including a therapy target. In addition, IMD 16 and/or programmer 14 may comprise data defining locations of therapy elements of IMD 16. Accordingly, GPU 124B may also produce a representation of the therapy elements of IMD 16 in the image produced by the rendering process.

In this manner, FIG. 6B represents an example of a device including a telemetry module configured to retrieve graphics processing data from a device that is not configured to perform a rendering process using the graphics processing data and that is associated with at least one of delivering therapy and sensing a physiological signal at a therapy target of a patient, and a control unit configured to apply the graphics processing data while performing the rendering process to generate an image of an anatomical feature of the patient, wherein the anatomical feature comprises the therapy target for an implantable medical device, and to cause a display unit of a user interface to display the image, wherein the image of the anatomical feature is specific to the patient. In the example of FIG. 6B, the graphics processing data comprises one or more transforms, and thus, the control unit is configured to obtain an anatomical atlas for the anatomical feature of the patient, wherein the anatomical atlas comprises a general model of the anatomical feature of the patient, apply the one or more transforms to the anatomical atlas to produce a patient-specific model of the anatomical feature of the patient, wherein the patient-specific model comprises three-dimensional graphics data, and render the patient-specific model to produce pixel data for the image representative of the patient-specific model.

FIG. 6C is a block diagram illustrating an example of image manipulation device 102C. Components of image manipulation device 102C that are named and numbered similarly to components of image manipulation device 102A of FIG. 6A conform substantially to the similarly named and numbered components. However, in this example, image manipulation device 102C does not include a patient-specific model generation unit. Furthermore, in this example, control unit 102C is configured to retrieve a list of vertices from IMD 16 and/or programmer 14 via telemetry module 126C. GPU 124C may render graphics objects comprising graphics primitives defined by the list of vertices to produce an image, and cause display 128C to display the image. In addition, IMD 16 and/or programmer 14 may comprise data defining locations of therapy elements of IMD 16. Accordingly, GPU 124C may also produce a representation of the therapy elements of IMD 16 in the image produced by the rendering process.

In this manner, FIG. 6C represents an example of a device including a telemetry module configured to retrieve graphics processing data from a device that is not configured to perform a rendering process using the graphics processing data and that is associated with at least one of delivering therapy and sensing a physiological signal at a therapy target of a patient, and a control unit configured to apply the graphics processing data while performing the rendering process to generate an image of an anatomical feature of the patient, wherein the anatomical feature comprises the therapy target for an implantable medical device, and to cause a display unit of a user interface to display the image, wherein the image of the anatomical feature is specific to the patient. In the example of FIG. 6C, the graphics processing data comprises a list of vertices for graphics primitives corresponding to a three-dimensional graphical mesh representative of the anatomical feature of the patient. Accordingly, the control unit, in this example, is configured to render the graphics primitives using the list of vertices to produce pixel data for the image representative of the graphics primitives of the three-dimensional graphical mesh.

Figure 7:
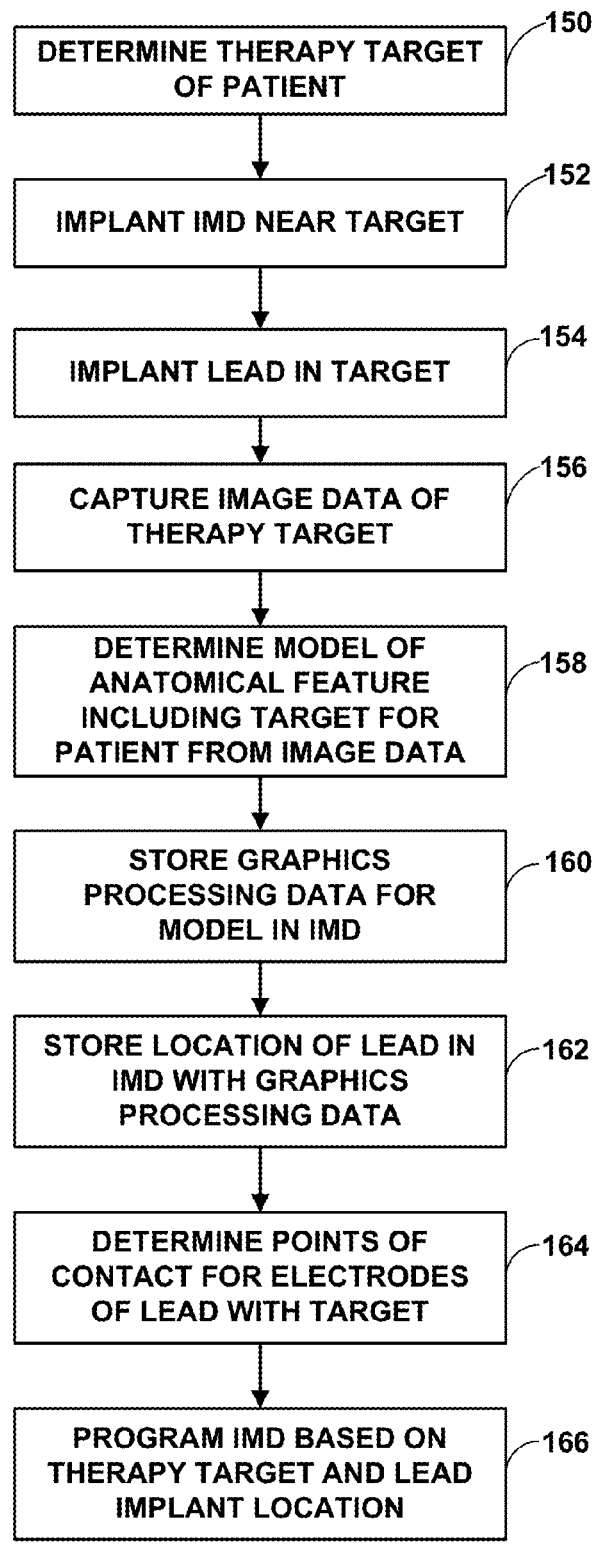
FIG. 7 is a flowchart illustrating an example method for storing graphics processing data to a device associated with delivering therapy to a patient.

FIG. 7 is a flowchart illustrating an example method for storing graphics processing data to a device associated with at least one of delivering therapy and sensing a physiological signal at a therapy target of a patient. Although discussed with respect to components of the example of FIG. 6A for purposes of example, it should be understood that steps of the method of FIG. 7 may be performed by other devices. For example, a clinician programmer, a patient programmer, a general purpose computer, or other device may be configured to perform steps of the method of FIG. 7. Moreover, certain steps of FIG. 7 may be omitted, performed in a different order or in parallel, and/or additional steps may be performed, without departing from the techniques of this disclosure.

Initially, a clinician may determine a therapy target of patient 12 (150). For example, the clinician or other medical personnel may diagnostically determine a therapy to be applied to patient 12, and that an implantable medical device, such as an implantable electrical stimulator or an implantable fluid delivery device, could be used to deliver the therapy. The clinician may then implant IMD 16 near the therapy target of patient 12 (152), and implant a therapy element, such as a lead, proximate to the therapy target (154).

Following the implant procedure, an imaging device, such as MRI unit 104, may capture image data of the therapy target of patient 12 (156). MRI unit 104 may, for example, capture a sequence of "slices" through magnetic resonance imaging procedures. Each of the slices may correspond to one image of a portion of the therapy target. MRI unit 104 may then provide the image data to image manipulation device 102A via MRI interface 118. Patient-specific model generation unit 130 of image manipulation device 102A may generate a patient-specific model of an anatomical feature that includes the therapy target for patient 12 from the received image data (158). For example, if an x-axis corresponds to the direction from one side of patient 12 to the other, a y-axis corresponds to the direction from the back of patient 12 to the front of patient 12, and the z-axis corresponds the direction from the head of patient 12 to the feet of patient 12, then each slice may include image data in x-y planes. Moreover, the slices may be stacked in z-axis order. In this manner, image analysis unit 116 may attempt to identify anatomical features in the slice-images received from MRI unit 104, while 3D model generation unit 114 may generate X- and Y-coordinates for the features within a particular slice, and Z-coordinates for the features based on the position of the feature in the ordering of the slices.

Using the patient-specific model, image manipulation device 102A may generate graphics processing data that, when applied during a rendering process, produces an image of the anatomical feature specific to patient 12. In some examples, the graphics processing data may comprise a list of vertices, while in other examples, the graphics processing data may comprise one or more transforms that can be applied to a non-patient-specific atlas, e.g., atlas model 120A. Image manipulation device 102A may then store the graphics processing data for the patient-specific model in, e.g., IMD 16 (160) via telemetry module 126A. Additionally or alternatively, image manipulation device 102A may store the graphics processing data to programmer 14. Moreover, programmer 14 need not necessarily be configured to perform the rendering process using the graphics processing data.

The image data provided by MRI unit 104 may also include a representation of a therapy element, such as one or more leads, of IMD 16, implanted within the therapy target of patient 12. Accordingly, image manipulation device 102A may also calculate data representative of the location of the therapy element and store the location data for the lead in IMD 16, along with the graphics processing data (162).

GPU 124A may further perform the rendering process to generate an image of the anatomical feature of patient 12 with a representation of the lead (or other therapy elements) of IMD 16 via display 128A. A clinician may use the image to determine, e.g., points of contact for electrodes of the lead with the therapy target (164). The clinician may determine a program (e.g., a combination of electrodes, stimulation frequency, pulse width, and/or amplitude, waveform, and the like) based at least in part on the image of the therapy target and the lead implant location presented in the image (166). The clinician may use image manipulation device 102A or another device to download the program to IMD 16, or to download an indication of a previously stored program for IMD 16 to use to deliver therapy to the therapy target of patient 12 via the therapy element (e.g., the lead).

In this manner, FIG. 7 represents an example of a method including obtaining information representative of an anatomical feature of a patient, wherein the anatomical feature comprises a therapy target for an implantable medical device, determining graphics processing data based on the obtained information, wherein the graphics processing data comprises data that, when applied during a rendering process, produces an image of the anatomical feature of the patient, and storing the graphics processing data to a device that is not configured to perform the rendering process using the graphics processing data, wherein the device is associated with at least one of delivering therapy and sensing a physiological signal at the therapy target of the patient.

Figure 8:
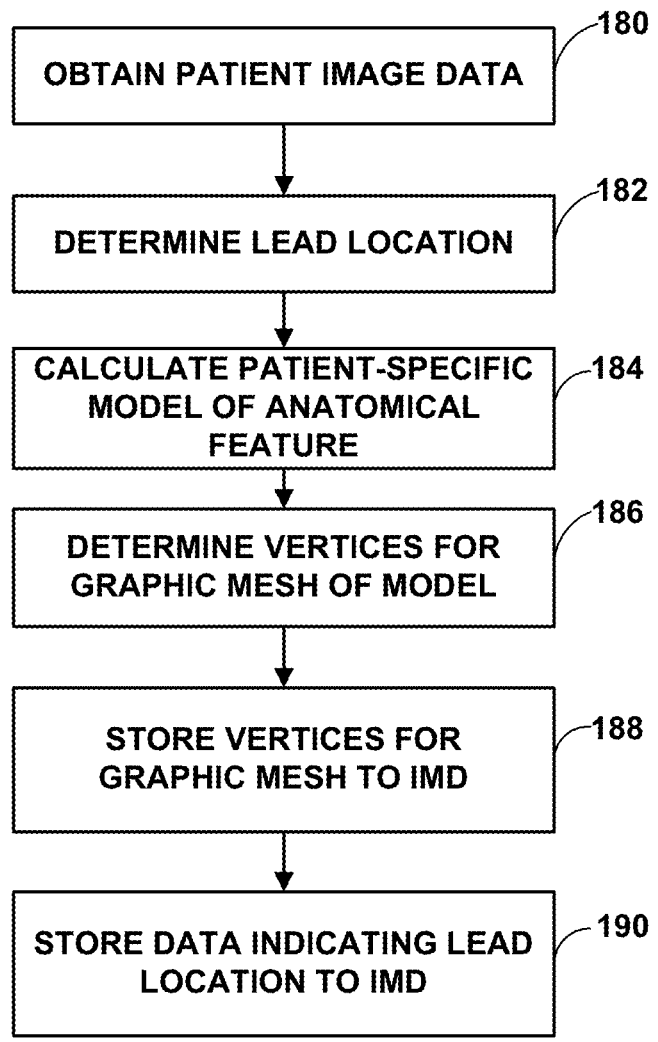
FIG. 8 is a flowchart illustrating an example method for creating and storing a list of vertices of graphics primitives to a device associated with delivering therapy to a patient.

FIG. 8 is a flowchart illustrating an example method for creating and storing a list of vertices of graphics primitives to a device associated with at least one of delivering therapy and sensing a physiological signal at a therapy target of a patient. Although discussed with respect to the example of image manipulation device 102A for purposes of example, it should be understood that the method of FIG. 8 may be performed by other devices. For example, a clinician programmer, a patient programmer, a general purpose computer, or other device may be configured to perform the method of FIG. 8. Moreover, certain steps of FIG. 8 may be omitted, performed in a different order or in parallel, and/or additional steps may be performed without departing from the techniques of this disclosure. Details of certain steps of FIG. 8 may conform substantially to similarly described steps of FIG. 7.

Initially, image manipulation device 102A may obtain image data of an anatomical feature of patient 12 (180). For example, as discussed above with respect to FIG. 7, image manipulation device 102A may receive image data from MRI unit 104. The image data may include an image of a lead or other therapy element of IMD 16. Using the image of the lead, image manipulation device 102A may determine a location of the lead in the therapy target of patient 12 (182).

3D model generation unit 114 may calculate a patient-specific model of an anatomical feature including the therapy target of patient 12 (184). 3D model generation unit 114 may determine a list of vertices defining graphics primitives of a graphic mesh of the patient-specific model (186). In the example of FIG. 8, image manipulation device 102A stores the list of vertices for the graphic mesh to IMD 16 (188). In other examples, image manipulation device 102A may store the list of vertices for the graphic mesh to programmer 14, in addition to or in the alternative to IMD 16. Image manipulation device 102A may also store data indication the location of the lead of IMD 16 to IMD 16 (190).

In this manner, FIG. 8 represents an example of a method including obtaining information representative of an anatomical feature of a patient, wherein the anatomical feature comprises a therapy target for an implantable medical device, determining graphics processing data based on the obtained information, wherein the graphics processing data comprises data that, when applied during a rendering process, produces an image of the anatomical feature of the patient, and storing the graphics processing data to a device that is not configured to perform the rendering process using the graphics processing data, wherein the device is associated with at least one of delivering therapy and sensing a physiological signal at the therapy target of the patient. In the example of FIG. 8, the graphics processing data includes a list of vertices for graphics primitives corresponding to a three-dimensional mesh based on the information representative of the anatomical feature of the patient.

Figure 9:
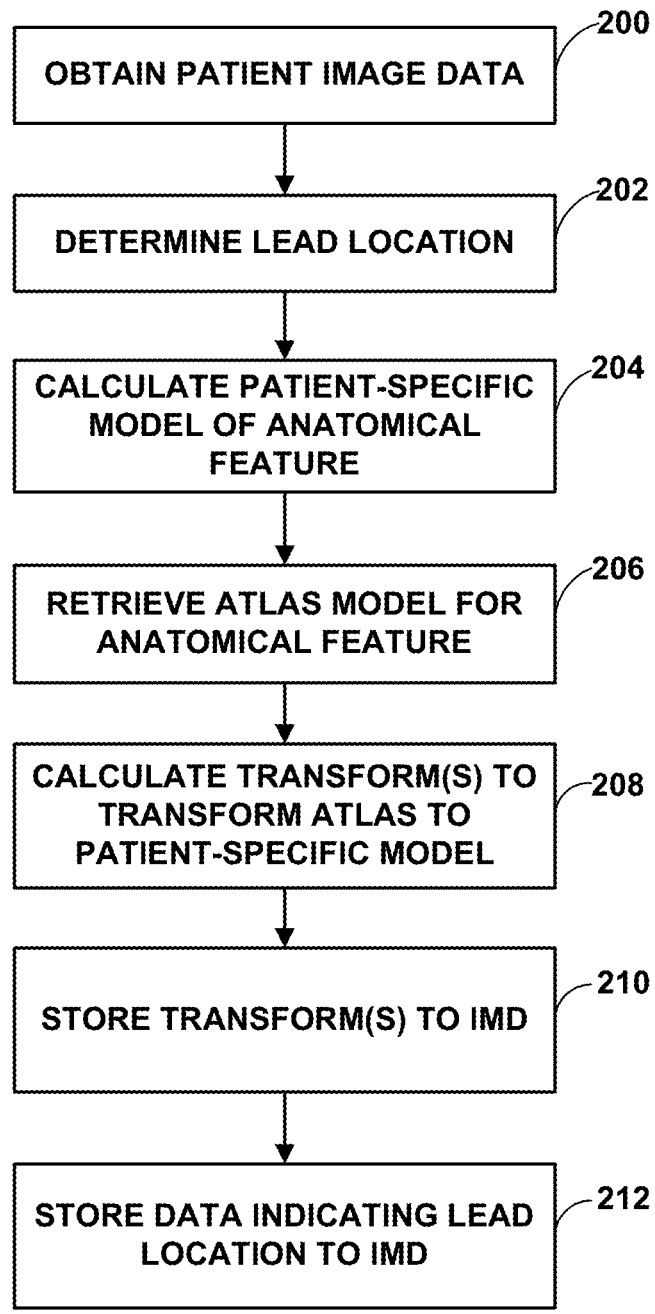
FIG. 9 is a flowchart illustrating an example method for creating and storing one or more transforms to a device associated with delivering therapy to a patient.

FIG. 9 is a flowchart illustrating an example method for creating and storing one or more transforms to a device associated with at least one of delivering therapy and sensing a physiological signal at a therapy target of a patient. Although discussed with respect to the example of image manipulation device 102A for purposes of example, it should be understood that the method of FIG. 9 may be performed by other devices. For example, a clinician programmer, a patient programmer, a general purpose computer, or other device may be configured to perform the method of FIG. 9. Moreover, certain steps of FIG. 9 may be omitted, performed in a different order or in parallel, and/or additional steps may be performed without departing from the techniques of this disclosure. Details of certain steps of FIG. 9 may conform substantially to similarly described steps of FIG. 7.

Initially, image manipulation device 102A may obtain image data of an anatomical feature of patient 12 (200). For example, as discussed above with respect to FIG. 7, image manipulation device 102A may receive image data from MRI unit 104. The image data may include an image of a lead or other therapy element of IMD 16. Using the image of the lead, image manipulation device 102A may determine a location of the lead in the therapy target of patient 12 (202). 3D model generation unit 114 may also calculate a patient-specific model of an anatomical feature including the therapy target of patient 12 (204).

In this example, 3D model generation unit 114 may provide the patient specific model to transform calculation unit 112. Transform calculation unit 112 may further retrieve data for atlas model 120A for the anatomical feature (206). However, whereas 3D model generation unit 114 provides a patient-specific model of the anatomical feature, atlas model 120A represents a non-patient-specific model of the anatomical feature. Transform calculation unit 112 may calculate one or more transforms that can be applied to transform atlas model 120A to a patient-specific model that is substantially similar to the patient-specific model received from 3D model generation unit 114 (208).

In this example, image manipulation device 102A may store the transforms calculated by transform calculation unit 112 to IMD 16 via telemetry module 126A (210). In addition, or in the alternative, image manipulation device 102A may store the transforms to programmer 14. Image manipulation device 102A may further store data indicating the lead location to IMD 16 and/or programmer 14 (212).

In this manner, FIG. 9 represents an example of a method including obtaining information representative of an anatomical feature of a patient, wherein the anatomical feature comprises a therapy target for an implantable medical device, determining graphics processing data based on the obtained information, wherein the graphics processing data comprises data that, when applied during a rendering process, produces an image of the anatomical feature of the patient, and storing the graphics processing data to a device that is not configured to perform the rendering process using the graphics processing data, wherein the device is associated with at least one of delivering therapy and sensing a physiological signal at the therapy target of the patient. In the example of FIG. 9, the graphics processing data includes one or more transforms that are applied to an anatomical atlas representing a general model of the anatomical feature of the patient. In this example, applying the one or more transforms to the anatomical atlas yields a patient-specific model that substantially conforms to the information representative of the anatomical feature of the patient.

Figure 10:
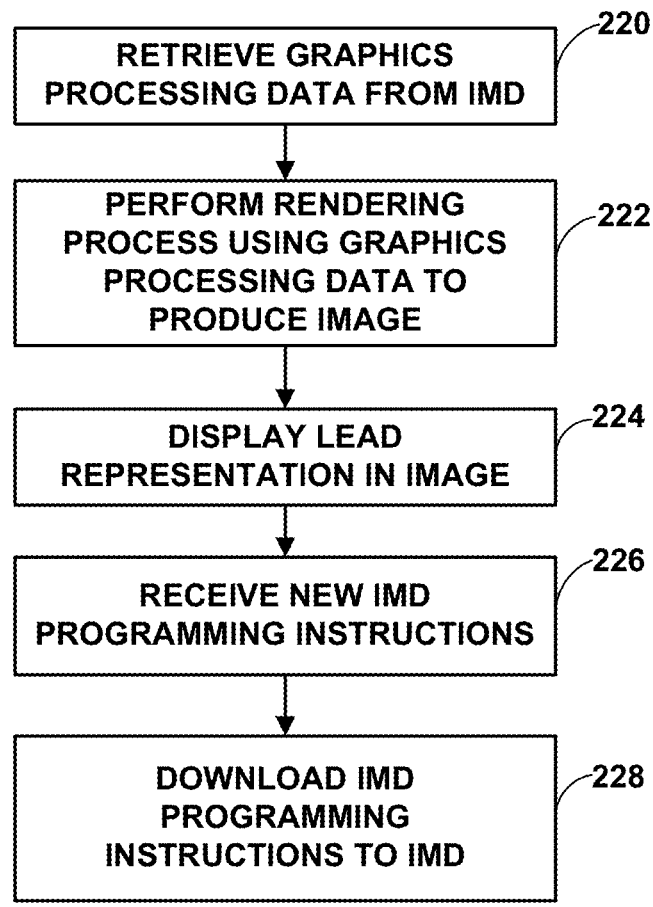
FIG. 10 is a flowchart illustrating an example method for retrieving graphics processing data from a device associated with delivering therapy to a patient and applying the graphics processing data during a rendering process to produce an image of an anatomical feature of the patient.

FIG. 10 is a flowchart illustrating an example method for retrieving graphics processing data from a device associated with at least one of delivering therapy and sensing a physiological signal at a therapy target of a patient and applying the graphics processing data during a rendering process to produce an image of an anatomical feature of the patient. Although discussed with respect to the example of image manipulation device 102A for purposes of example, it should be understood that the method of FIG. 10 may be performed by other devices. For example, a clinician programmer, a patient programmer (when configured to perform a rendering process), a general purpose computer, or other device may be configured to perform the method of FIG. 10. Moreover, certain steps of FIG. 10 may be omitted, performed in a different order or in parallel, and/or additional steps may be performed without departing from the techniques of this disclosure.

Initially, image manipulation device 102A may retrieve graphics processing data, such as a list of vertices or one or more transforms, from IMD 16 (220). In other examples, image manipulation device 102A may retrieve the graphics processing data from a patient programmer, such as programmer 14. GPU 124A may then perform a rendering process using the retrieved graphics processing data to produce an image of the patient-specific anatomical feature of patient 12 (222). For example, when the graphics processing data comprises a list of vertices, GPU 124A may render a graphics object comprising graphics primitives defined by the list of vertices to produce the image. When the graphics processing data comprises one or more transforms, GPU 124A may apply the transforms to atlas model 120A to produce a patient-specific model, which GPU 124A may render to produce the image.

During the rendering process, GPU 124A may also utilize data indicative of a location of a lead (or other therapy element) of IMD 16 to display a representation of the lead in the image (224). For example, the graphics processing data may comprise data for a first graphics object corresponding to the patient-specific anatomical feature, and a second graphics object corresponding to the lead (or other therapy element). When performing the rendering process, GPU 124A may render both of these graphics objects to produce an image of the anatomical feature as well as the lead (or other therapy element) of IMD 16.

In the example of FIG. 10, a clinician may review the image, in addition to other data, e.g., patient feedback data, to determine the location of the lead in the therapy target of patient 12. Based on the information available, the clinician may determine whether IMD 16 should be reprogrammed, or whether IMD 16 should be configured to operate according to a different program already stored by IMD 16. Accordingly, image manipulation device 102A (which may, in this example, comprise a clinician programmer) may receive new IMD programming instructions (226), e.g., from the clinician, and download the new IMD programming instructions to IMD 16 (228). Of course, if the clinician determines that no new programming instructions are needed, steps 226 and 228 may be omitted.

In this manner, FIG. 10 represents an example of a method including retrieving graphics processing data from a device that is not configured to perform a rendering process using the graphics processing data, wherein the device is associated with at least one of delivering therapy and sensing a physiological signal at a therapy target of a patient, applying the graphics processing data while performing the rendering process to generate an image of an anatomical feature of the patient, wherein the anatomical feature comprises the therapy target for an implantable medical device, and displaying the image, wherein the image of the anatomical feature is specific to the patient.

Figure 11:
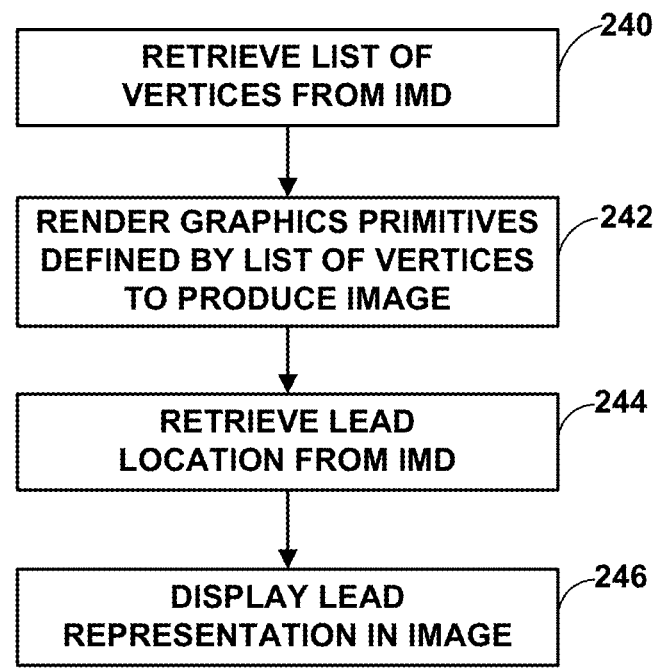
FIG. 11 is a flowchart illustrating an example method for retrieving and rendering a list of vertices of graphics primitives stored by a device associated with delivering therapy to a patient to produce an image of an anatomical feature of the patient.

FIG. 11 is a flowchart illustrating an example method for retrieving and rendering a list of vertices of graphics primitives stored by a device associated with at least one of delivering therapy and sensing a physiological signal at a therapy target of a patient to produce an image of an anatomical feature of the patient. Although discussed with respect to the example of image manipulation device 102C for purposes of example, it should be understood that the method of FIG. 11 may be performed by other devices. For example, image manipulation device 102A, a clinician programmer, a patient programmer (when configured to perform a rendering process), a general purpose computer, or other device may be configured to perform the method of FIG. 11. Moreover, certain steps of FIG. 11 may be omitted, performed in a different order or in parallel, and/or additional steps may be performed without departing from the techniques of this disclosure. Details of certain steps of FIG. 11 may conform substantially to similarly described steps of FIG. 10.

In this example, image manipulation device 102C may retrieve a list of vertices from IMD 16 (or in some examples, programmer 14) (240). The list of vertices may define one or more graphics primitives for a graphics object corresponding to a patient-specific model of an anatomical feature of patient 12. Accordingly, GPU 124C may render the graphics primitives defined by the list of vertices to produce an image specific to the anatomical feature of patient 12 (242). Image manipulation unit 102C may also retrieve lead location data from IMD 16 (244) and display a lead representation in the image (246).

Although illustrated as separate steps, it should be understood that, in general, a graphics object representative of the lead and one or more graphics objects representative of the patient-specific model of the anatomical feature may be rendered as part of the same rendering process. The steps in FIG. 11 are illustrated separately only for purposes of example. Thus, the final image produced by the rendering process may include a representation of the patient-specific anatomical feature, as well as a representation of the lead (or, in other examples, other therapy elements, such as one or more leads or one or more catheters).

In this manner, FIG. 11 represents an example of a method including retrieving graphics processing data from a device that is not configured to perform a rendering process using the graphics processing data, wherein the device is associated with at least one of delivering therapy and sensing a physiological signal at a therapy target of a patient, applying the graphics processing data while performing the rendering process to generate an image of an anatomical feature of the patient, wherein the anatomical feature comprises the therapy target for an implantable medical device, and displaying the image, wherein the image of the anatomical feature is specific to the patient. In the example of FIG. 11, the graphics processing data corresponds to a list of vertices for graphics primitives corresponding to a three-dimensional graphical mesh representative of the anatomical feature of the patient. The method may therefore include rendering the graphics primitives using the list of vertices to produce pixel data for the image representative of the graphics primitives of the three-dimensional graphical mesh.

Figure 12:
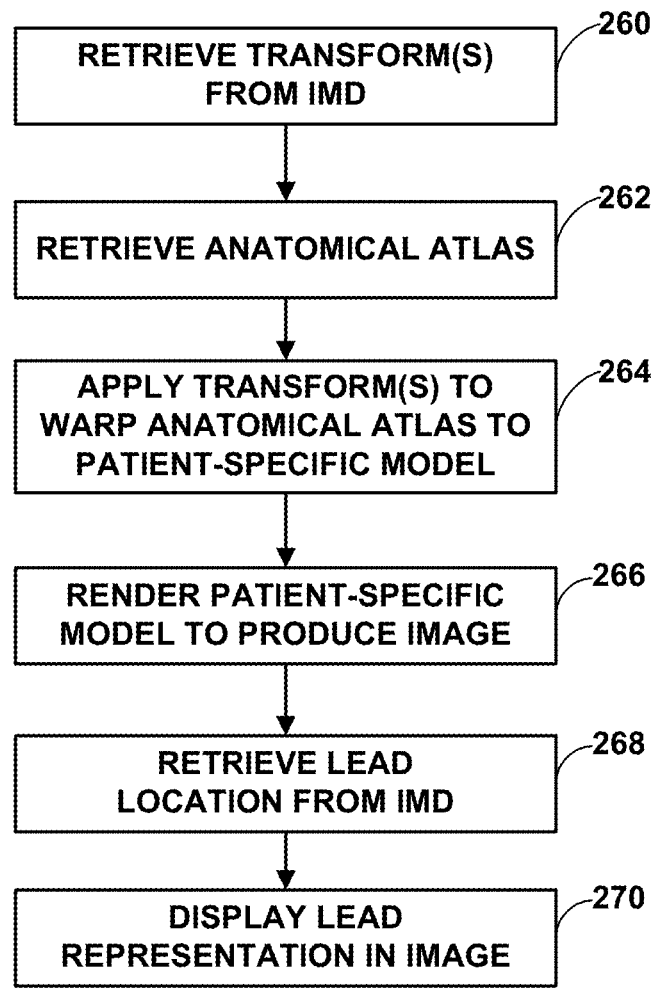
FIG. 12 is a flowchart illustrating an example method for retrieving one or more transforms stored by a device associated with delivering therapy to a patient and applying the matrices to warp an anatomical atlas for an anatomical feature of the patient to produce a patient-specific image of the anatomical feature.

FIG. 12 is a flowchart illustrating an example method for retrieving one or more transforms stored by a device associated with at least one of delivering therapy and sensing a physiological signal at a therapy target of a patient and applying the matrices to warp an anatomical atlas for an anatomical feature of the patient to produce a patient-specific image of the anatomical feature. Although discussed with respect to the example of image manipulation device 102B for purposes of example, it should be understood that the method of FIG. 12 may be performed by other devices. For example, image manipulation device 102A, a clinician programmer, a patient programmer (when configured to perform a rendering process), a general purpose computer, or other device may be configured to perform the method of FIG. 12. Moreover, certain steps of FIG. 12 may be omitted, performed in a different order or in parallel, and/or additional steps may be performed without departing from the techniques of this disclosure. Details of certain steps of FIG. 12 may conform substantially to similarly described steps of FIG. 10.

In this example, image manipulation device 102B may retrieve one or more transforms from IMD 16 (or in some examples, programmer 14) (260). GPU 124B may retrieve data for atlas model 120B, which comprises a non-patient-specific anatomical atlas in this example (262). GPU 124B may apply the retrieved transforms to data for atlas model 120B to warp the anatomical atlas to a patient-specific model (264). GPU 124B may also render the patient-specific model to produce a patient-specific model of the anatomical feature of patient 12 (266). Image manipulation unit 102B may also retrieve lead location data from IMD 16 (268) and display a lead representation in the image (270). As discussed with respect to the method of FIG. 11, it should be understood that, in general, a graphics object representative of the lead and one or more graphics objects representative of the patient-specific model of the anatomical feature may be rendered as part of the same rendering process, rather than as separate steps as illustrated in the example of FIG. 12. Again, FIG. 12 provides separate steps for purpose of explanation.

In this manner, FIG. 12 represents an example of a method including retrieving graphics processing data from a device that is not configured to perform a rendering process using the graphics processing data, wherein the device is associated with at least one of delivering therapy and sensing a physiological signal at a therapy target of a patient, applying the graphics processing data while performing the rendering process to generate an image of an anatomical feature of the patient, wherein the anatomical feature comprises the therapy target for an implantable medical device, and displaying the image, wherein the image of the anatomical feature is specific to the patient. In the example of FIG. 12, the graphics processing data corresponds to one or more transforms that, when applied to the anatomical atlas, produce a patient-specific model of the anatomical feature of the patient. The method may therefore include rendering the patient-specific model to produce pixel data for the image representative of the patient-specific model.

Figure 13:
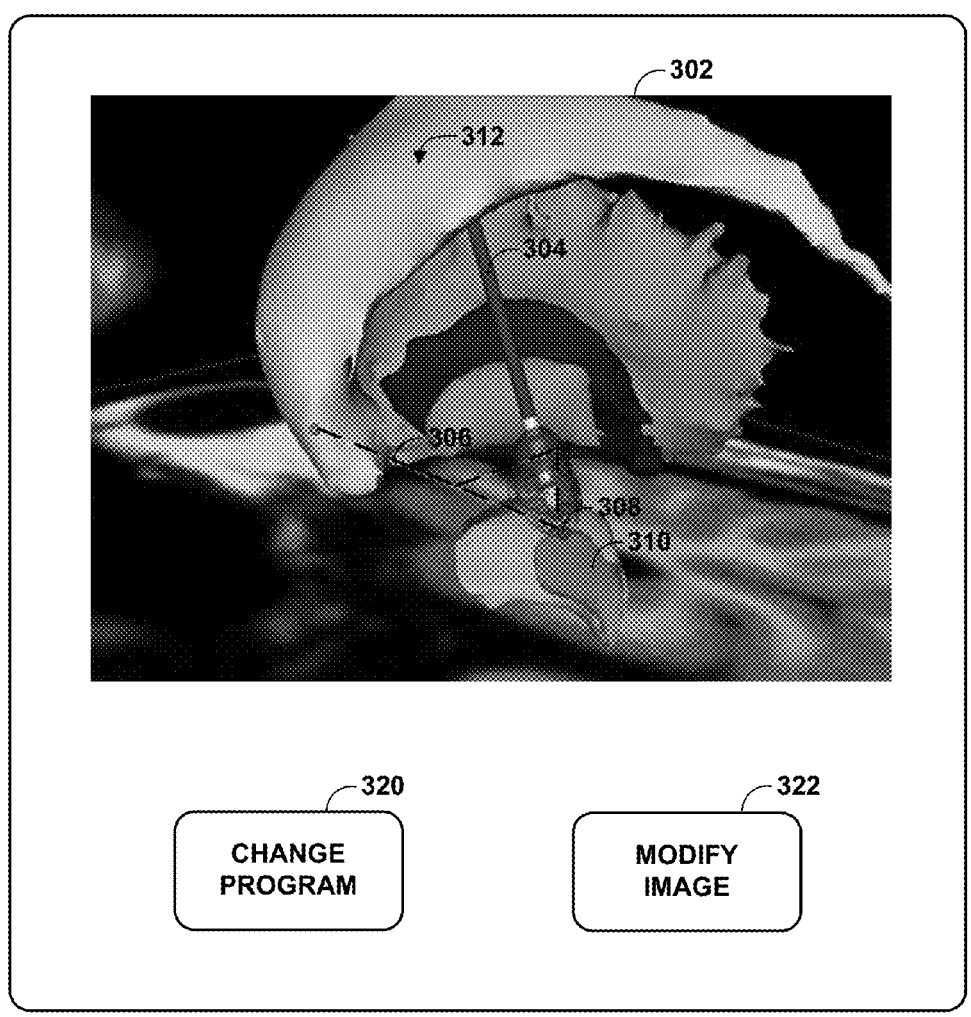
FIG. 13 is a conceptual diagram illustrating an example graphical user interface displaying an example patient-specific image of an anatomical feature of a patient.

FIG. 13 is a conceptual diagram illustrating an example graphical user interface 300 displaying an example patient-specific image 302 of an anatomical feature 312 of patient 12. In this example, anatomical feature 312 corresponds to a portion of brain 28 of patient 12. Image 302, in this example, also includes a graphical representation of a lead 304. Lead 304 includes distal tip 308 implanted near therapy target 310. Dashed lines 306 (which would not necessarily be illustrated in image 302) are representative of an angle of lead 304 relative to distal tip 308 of lead 304. User interface 300 may be referred to as a visualization interface or a visualization programming interface for DBS programming.

User interface 300 also provides change program button 320 and modify image button 322. When a clinician or other user selects change program button 320 (e.g., using a mouse, a stylus, a finger (with a touchpad device), or other input mechanism), a computing device presenting user interface 300 may provide a separate window (not shown) by which the user may modify programming of IMD 16. Using this separate window, the user may adjust various programming parameters of IMD 16, e.g., to select a different program stored on IMD 16 or to define a new program for IMD 16.

When a clinician or other user selects modify image button 322, a computing device presenting user interface 300 may provide a separate window (not shown) by which the user may modify a view of anatomical feature 312 and lead 304. For example, the user may adjust camera parameters (such as camera position and/or camera direction) relative to anatomical feature 312 and lead 304. A GPU of a computing device presenting user interface 300 may re-render data using the same graphics processing data used to generate image 302 based on the new camera parameters, to generate a second, different image of anatomical feature 312 and lead 304.

As another example, the user may highlight various graphical objects of image 302 using, e.g., various colors, hide graphics objects of image 302 (e.g., hide lead 304 or electrodes thereof, or other objects for anatomical feature 312 not of interest, e.g., to avoid occlusion), or otherwise manipulate the displayed image to gain a fuller appreciation of the idiosyncratic elements of anatomical feature 312 specific to patient 12, in order to better treat patient 12.

In still other examples, the separate window may allow the user to retrieve a second image of anatomical feature 312, e.g., an image generated according to a second, different patient-specific model, which may have been created at a different time as the model used to generate image 302. In this manner, the user may compare the two images to determine changes to anatomical feature 312 and/or lead 304, e.g., to detect lead migration.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer-readable media may include non-transitory computer-readable storage media and transient communication media. Computer readable storage media, which is tangible and non-transitory, may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer-readable storage media. It should be understood that the term "computer-readable storage media" refers to physical storage media, and not signals, carrier waves, or other transient media.

Various examples have been described. These and other examples are within the scope of the following claims.

The invention claimed is:

1. A method comprising:
    obtaining, via an interface, information representative of an anatomical feature of a patient, wherein the anatomical feature comprises a therapy target for an implantable medical device;
    determining graphics processing data based on the obtained information, wherein the graphics processing data comprises data that, when applied during a rendering process, produces an image of the anatomical feature of the patient; and
    storing the graphics processing data to a device that is not configured to perform the rendering process using the graphics processing data, wherein the device is configured to at least one of deliver therapy and sense a physiological signal at the therapy target of the patient.

2. The method of claim 1, wherein storing the graphics processing data to the device comprises at least one of storing the graphics processing data to the implantable medical device and storing the graphics processing data to a patient programmer device associated with the implantable medical device.

3. The method of claim 1, wherein obtaining the information comprises receiving at least one of magnetic resonance imaging (MRI) data and computed tomography (CT) data for the anatomical feature of the patient.

4. The method of claim 1, wherein determining the graphics processing data comprises:
    calculating a three-dimensional mesh based on the information representative of the anatomical feature; and
    generating a list of vertices for graphics primitives corresponding to the mesh, wherein the graphics processing data comprises the list of vertices.

5. The method of claim 1, wherein determining the graphics processing data comprises:
    retrieving an anatomical atlas for the anatomical feature of the patient, wherein the anatomical atlas comprises a general model of the anatomical feature of the patient; and
    calculating one or more transforms that, when applied to the anatomical atlas, produce a patient-specific model that substantially conforms to the information representative of the anatomical feature of the patient, wherein the graphics processing data comprises the one or more transforms.

6. The method of claim 1, further comprising storing information representative of a location of a therapy element at the therapy target to the device, wherein the implantable medical device is coupled to the therapy element and is configured to deliver therapy to the therapy target via the therapy element.

7. The method of claim 6, wherein the therapy element comprises one of a lead and a catheter, and wherein storing the information representative of the location of the therapy element comprises:
    storing vertex data representative of a location of a distal tip of the therapy element to the device;
    storing an angle value for the therapy element relative to the location of the distal tip to the device; and
    storing an indication of at least one of an axial rotation and an orientation of the therapy element.

8. The method of claim 6, wherein the therapy element comprises a lead, and wherein storing the information representative of the location of the therapy element comprises:
    storing vertex data representative of centers of electrodes along the lead to the device.

9. A device comprising:
    an interface configured to obtain information representative of an anatomical feature of a patient, wherein the anatomical feature comprises a therapy target for an implantable medical device; and
    a control unit configured to determine graphics processing data based on the obtained information, wherein the graphics processing data comprises data that, when applied during a rendering process, produces an image of the anatomical feature of the patient, and store the graphics processing data to a device that is not configured to perform the rendering process using the graphics processing data, wherein the device is configured to at least one of deliver therapy and sense a physiological signal at the therapy target of the patient.

10. The device of claim 9, wherein to determine the graphics processing data, the control unit is configured to calculate a three-dimensional mesh based on the information representative of the anatomical feature, and generate a list of vertices for graphics primitives corresponding to the mesh, wherein the graphics processing data comprises the list of vertices.

11. The device of claim 9, wherein to determine the graphics processing data, the control unit is configured to obtain an anatomical atlas for the anatomical feature of the patient, wherein the anatomical atlas comprises a general model of the anatomical feature of the patient, and calculate one or more transforms that, when applied to the anatomical atlas, produce a patient-specific model that substantially conforms to the information representative of the anatomical feature of the patient, wherein the graphics processing data comprises the one or more transforms.

12. The device of claim 9, wherein the control unit is configured to store information representative of a location of a therapy element at the therapy target to the device, wherein the implantable medical device is coupled to the therapy element and is configured to deliver therapy to the therapy target via the therapy element.

13. The device of claim 12, wherein the therapy element comprises one of a lead and a catheter, and wherein to store the information representative of the location of the therapy element, the control unit is configured to store vertex data representative of a location of a distal tip of the therapy element to the device, store an angle value for the therapy element relative to the location of the distal tip to the device, and store an indication of at least one of an axial rotation and an orientation of the therapy element.

14. The device of claim 12, wherein the therapy element comprises a lead, and wherein to store the information representative of the location of the therapy element, the control unit is configured to store vertex data representative of centers of electrodes along the lead to the device.

15. A non-transitory computer-readable storage medium comprising instructions that, when executed, cause a processor to:
    obtain, via an interface, information representative of an anatomical feature of a patient, wherein the anatomical feature comprises a therapy target for an implantable medical device;
    determine graphics processing data based on the obtained information, wherein the graphics processing data comprises data that, when applied during a rendering process, produces an image of the anatomical feature of the patient; and
    store the graphics processing data to a device that is not configured to perform the rendering process using the graphics processing data, wherein the device is configured to at least one of deliver therapy and sense a physiological signal at the therapy target of the patient.

16. The computer-readable storage medium of claim 15, wherein the instructions that cause the processor to determine the graphics processing data comprise instructions that cause the processor to:
   calculate a three-dimensional mesh based on the information representative of the anatomical feature; and
   generate a list of vertices for graphics primitives corresponding to the mesh, wherein the graphics processing data comprises the list of vertices.

17. The computer-readable storage medium of claim 15, wherein the instructions that cause the processor to determine the graphics processing data comprise instructions that cause the processor to:
   retrieve an anatomical atlas for the anatomical feature of the patient, wherein the anatomical atlas comprises a general model of the anatomical feature of the patient; and
   calculate one or more transforms that, when applied to the anatomical atlas, produce a patient-specific model that substantially conforms to the information representative of the anatomical feature of the patient, wherein the graphics processing data comprises the one or more transforms.

18. The computer-readable storage medium of claim 15, further comprising instructions that cause the processor to store information representative of a location of a therapy element at the therapy target to the device, wherein the implantable medical device is coupled to the therapy element and is configured to deliver therapy to the therapy target via the therapy element.

19. The computer-readable storage medium of claim 18, wherein the therapy element comprises one of a lead and a catheter, and wherein the instructions that cause the processor to store the information representative of the location of the therapy element comprise instructions that cause the processor to:
   store vertex data representative of a location of a distal tip of the therapy element to the device;
   store an angle value for the therapy element relative to the location of the distal tip to the device; and
   store an indication of at least one of an axial rotation and an orientation of the therapy element.

20. The computer-readable storage medium of claim 18, wherein the therapy element comprises a lead, and wherein the instructions that cause the processor to store the information representative of the location of the therapy element comprise instructions that cause the processor to:
   store vertex data representative of centers of electrodes along the lead to the device.

* * * * *